United States Patent
Hiddessen et al.

(10) Patent No.: US 11,060,136 B2
(45) Date of Patent: *Jul. 13, 2021

(54) EMULSION CHEMISTRY FOR ENCAPSULATED DROPLETS

(71) Applicant: Bio-Rad Laboratories, Inc., Hercules, CA (US)

(72) Inventors: Amy L. Hiddessen, Dublin, CA (US); Benjamin J. Hindson, Livermore, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 68 days.

This patent is subject to a terminal disclaimer.

(21) Appl. No.: 16/447,315

(22) Filed: Jun. 20, 2019

(65) Prior Publication Data

US 2019/0316191 A1    Oct. 17, 2019

Related U.S. Application Data

(63) Continuation of application No. 15/452,582, filed on Mar. 7, 2017, now Pat. No. 10,378,048, which is a continuation of application No. 12/976,827, filed on Dec. 22, 2010, now Pat. No. 9,598,725.

(60) Provisional application No. 61/417,241, filed on Nov. 25, 2010, provisional application No. 61/410,769, filed on Nov. 5, 2010, provisional application No. 61/409,473, filed on Nov. 2, 2010, provisional application No. 61/409,106, filed on Nov. 1, 2010, provisional application No. 61/380,981, filed on Sep. 8, 2010, provisional application No. 61/317,635, filed on Mar. 25, 2010, provisional application No. 61/341,218, filed on Mar. 25, 2010, provisional application No. 61/309,845, filed on Mar. 2, 2010.

(51) Int. Cl.
```
C12Q 1/68       (2018.01)
C12Q 1/6848     (2018.01)
C12Q 1/6844     (2018.01)
C12Q 1/6816     (2018.01)
C12Q 1/686      (2018.01)
```

(52) U.S. Cl.
CPC ........... *C12Q 1/6848* (2013.01); *C12Q 1/686* (2013.01); *C12Q 1/6816* (2013.01); *C12Q 1/6846* (2013.01)

(58) Field of Classification Search
CPC ........... C12Q 1/6816; C12Q 1/6846; C12Q 2527/125; C12Q 2563/159; C12Q 1/686; C12Q 1/6848
See application file for complete search history.

(56) References Cited

U.S. PATENT DOCUMENTS

| | | |
|---|---|---|
| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 4,990,283 A | 2/1991 | Visca et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |

(Continued)

FOREIGN PATENT DOCUMENTS

| | | |
|---|---|---|
| EP | 1 522 582 A2 | 4/2005 |
| EP | 1 522 582 B1 | 4/2007 |

(Continued)

OTHER PUBLICATIONS

J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.

(Continued)

*Primary Examiner* — David C Thomas
(74) *Attorney, Agent, or Firm* — Kilpatrick Townsend and Stockton LLP

(57) ABSTRACT

System, including methods, apparatus, compositions, and kits, for making and using a stabilized emulsion. A method of generating a stabilized emulsion is provided. In the method, an aqueous phase may be provided. The aqueous phase may include an effective concentration of one or more skin-forming proteins. An emulsion may be formed. The emulsion may include droplets of a dispersed phase disposed in a continuous phase, with the aqueous phase being the continuous phase or the dispersed phase. The emulsion may be heated to create an interfacial skin between each droplet and the continuous phase, to transform the droplets into capsules.

13 Claims, 4 Drawing Sheets

(56) References Cited

U.S. PATENT DOCUMENTS

| | | |
|---|---|---|
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 9,562,837 B2 * | 2/2017 | Link ..................... B03C 5/026 |
| 9,598,725 B2 | 3/2017 | Hiddessen et al. |
| 10,378,048 B2 * | 8/2019 | Hiddessen ............. C12Q 1/686 |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |

(56) References Cited

U.S. PATENT DOCUMENTS

| | | |
|---|---|---|
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamaish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |
| 2013/0288254 A1 | 10/2013 | Pollack et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | WO 82/02562 | 8/1982 |
| WO | WO 84/02000 | 5/1984 |
| WO | WO 92/01812 | 2/1992 |
| WO | WO 94/05414 | 3/1994 |
| WO | WO 96/12194 | 4/1996 |
| WO | WO 98/00231 | 1/1998 |
| WO | WO 98/16313 | 4/1998 |
| WO | WO 98/44151 | 10/1998 |
| WO | WO 98/44152 | 10/1998 |
| WO | WO 98/47003 | 10/1998 |
| WO | WO 01/07159 | 2/2001 |
| WO | WO 01/12327 | 2/2001 |
| WO | WO 01/94001 A2 | 12/2001 |
| WO | WO 02/23163 | 3/2002 |
| WO | WO 02/060584 | 8/2002 |
| WO | WO 02/068104 | 9/2002 |
| WO | WO 02/081490 | 10/2002 |
| WO | WO 02/081729 | 10/2002 |
| WO | WO 03/006151 A1 | 1/2003 |
| WO | WO 03/016558 | 2/2003 |
| WO | WO 03/042410 | 5/2003 |
| WO | WO 03/072258 | 9/2003 |
| WO | WO 2004/040001 | 5/2004 |
| WO | WO 2005/007812 | 1/2005 |
| WO | WO 2005/010145 | 2/2005 |
| WO | WO 2005/021151 | 3/2005 |
| WO | WO 2005/023091 | 3/2005 |
| WO | WO 2005/048227 A2 | 5/2005 |
| WO | WO 2005/055807 | 6/2005 |
| WO | WO 2005/073410 | 8/2005 |
| WO | WO 2005/075683 | 8/2005 |
| WO | WO 2006/023719 | 3/2006 |
| WO | WO 2006/027757 | 3/2006 |

(56) References Cited

FOREIGN PATENT DOCUMENTS

| WO | WO 2006/038035 | 4/2006 |
|---|---|---|
| WO | WO 2006/086777 | 8/2006 |
| WO | WO 2006/095981 | 9/2006 |
| WO | WO 2007/091228 | 8/2007 |
| WO | WO 2007/091230 | 8/2007 |
| WO | WO 2007/092473 | 8/2007 |
| WO | WO 2007/096592 A1 | 8/2007 |
| WO | WO 2007/120241 A2 | 10/2007 |
| WO | WO 2007/133710 | 11/2007 |
| WO | WO 2008/021123 | 2/2008 |
| WO | WO 2008/024114 | 2/2008 |
| WO | WO 2008/063227 | 5/2008 |
| WO | WO 2008/070074 | 6/2008 |
| WO | WO 2008/070862 | 6/2008 |
| WO | WO 2008/109176 | 9/2008 |
| WO | WO 2008/109878 | 9/2008 |
| WO | WO 2008/112177 | 9/2008 |
| WO | WO 2009/002920 | 12/2008 |
| WO | WO 2009/015863 | 2/2009 |
| WO | WO 2009/049889 | 4/2009 |
| WO | WO 2009/085246 | 7/2009 |
| WO | WO 2010/001419 | 1/2010 |
| WO | WO 2010/018465 | 2/2010 |
| WO | WO 2011/034621 | 3/2011 |
| WO | WO 2011/079176 | 6/2011 |

OTHER PUBLICATIONS

A. Chittofrati et al., "Perfluoropolyether microemulsions," Progress in Colloid & Polymer Science 79, pp. 218-225, (1989).
Steven A. Snow, "Synthesis and Characterization of Zwitterionic Silicone Sulfobetaine Surfactants," Langmuir, vol. 6, No. 2, American Chemical Society, pp. 385-391, (1990).
Polydimethylsiloxane, 5 pgs., published in FNP 52 (1992).
Russell Higuchi et al., "Kinetic PCR Analysis: Real-time Monitoring of DNA Amplification Reactions," Bio/Technology vol. II, pp. 1026-1030, Sep. 11, 1993.
D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).
Y. Sela et al., "Newly designed polysiloxane-graft-poly(oxyethylene) copolymeric surfactants: preparation, surface activity and emulsification properties," Colloid & Polymer Science 272, pp. 684-691, (1994).
M. Gasperlin et al., "The structure elucidation of semisolid w/o emulsion systems containing silicone surfactant," International Journal of Pharmaceutics 107, pp. 51-56, (1994).
Mieczyslaw A. Piatyszek et al., "Detection of telomerase activity in human cells and tumors by a telomeric repeat amplification protocol (TRAP)," Methods in Cell Science 17, pp. 1-15, (1995).
Anthony P. Shuber et al., "A Simplified Procedure for Developing Multiplex PCRs," Genome Research, published by Cold Spring Harbor Laboratory Press, pp. 488-493, (1995).
A. V. Yazdi et al., "Highly Carbon Dioxide Soluble Surfactants, Dispersants and Chelating Agents," Fluid Phase Equilibria, vol. 117, pp. 297-303, (1996).
Ariel A. Avilion et al., "Human Telomerase RNA and Telomerase Activity in Immortal Cell Lines and Tumor Tissues," Cancer Research 56, pp. 645-650, Feb. 1, 1996.
Shuming Nie et al., "Optical Detection of Single Molecules," Annu. Rev. Biophys. BiomoL Struct. vol. 26, pp. 567-596, (1997).
Edith J. Singley et al., "Phase behavior and emulsion formation of novel fluoroether amphiphiles in carbon dioxide," Fluid Phase Equilibria 128, pp. 199-219, (1997).
Olga Kalinina et al., "Nanoliter scale PCR with TagMan Detection," Nucleic Acids Research, vol. 25, No. 10 pp. 1999-2004, (1997).
Zhen Guo et al., "Enhanced discrimination of single nucleotide polymorphisms by artificial mismatch hybridization," Nature Biotechnology vol. 15, pp. 331-335, Apr. 1997.
E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Bert Vogelstein et al., "Digital PCR," Proc. Natl. Acad. Sci. USA, vol. 96, pp. 9236-9241, Aug. 1999.
Anthony J. O'Lenick, Jr., "Silicone Emulsions and Surfactants," Journal of Surfactants and Detergents, vol. 3, No. 3, Jul. 2000.
N. Garti et al., "Water Solubilization in Nonionic Microemulsions Stabilized by Grafted Siliconic Emulsifiers," Journal of Colloid and Interface Science vol. 233, pp. 286-294, (2001).
Shinji Katsura et al., "Indirect micromanipulation of single molecules in water-in-oil emulsion," Electrophoresis, vol. 22, pp. 289-293, (2001).
Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).
Hidenori Nagai et al., Development of a Microchamber Array for. Picoliter PCR, Analytical Chemistry, vol. 73, No. 5, pp. 1043-1047, Mar. 1, 2001.
Christopher B. Price, "Regular Review Point of Care Testing," BMJ, vol. 322, May 26, 2001.
3M Specialty Materials, "3M Fluorinert Electronic Liquid FC-3283," product information guide, issued Aug. 2001.
Ivonne Schneega13 et al., "Miniaturized flow-through PCR with different template types in a silicon chip thermocycler," Lab on a Chip, vol. 1, pp. 4249, (2001).
Randla M. Hill, "Silicone surfactants—new developments," Current Opinion in Colloid & Interface Science 7, pp. 255-261, (2002).
Richard M. Cawthon, "Telomere measurement by quantitative PCR," Nucleic Acids Research, vol. 30, No. 10, pp. 1-6, (2002).
Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331340 (2002).
Shelley L. Anna et al., "Formation of dispersions using "flow focusing" in microchannels," Applied Physics Letters, vol. 82, No. 3, Jan. 20, 2003.
Goldschmidt GMBH, "Abil® EM 90 Emulsifier for the formulation of cosmetic W/O creams and lotions," degussa. creating essentials brochure, pp. 1-7, May 2003.
Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Dev1n Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stephane Swillens et al., "Instant evaluation of the absolute initial number of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.

(56) References Cited

OTHER PUBLICATIONS

Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 37063715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).
Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
John H. Leamon et al., "Overview: methods and applications for droplet compartmentalization of biology," Nature Methods, vol. 3, No. 7, pp. 541543, Jul. 2006.
Andrew D. Griffiths et al., "Miniaturising the laboratory in emulsion droplets," Trends in Biotechnology, vol. 24, No. 9, pp. 395-402, Jul. 14, 2006.
Jian-Blng Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.

Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Diehl et al. (2006) nature Methods, vol. 3, No. 7, pp. 551-559, DOI:10. 1038/NMETH898.
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jln et al., "Practical Time-Gated Luminescence Flow Cytometry. II: Experimental Evaluation Using UV LED Excitation," Cytometry Part A • 71A, pp. 797-808, Aug. 24, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.
Nicole Pamme, "continuous flow separations in microfluidic devices," Lab on a Chip, vol. 7, pp. 1644-1659, Nov. 2, 2007.
N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.

(56) References Cited

OTHER PUBLICATIONS

Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hs1n Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics." Lanamuir. vol. 24. No. 12. pus. 6382-6289. May 16.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Jian Qin et al., "Studying copy number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 43204323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.

Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semi-solid Polymer Interphase," Langmuir, ACS Publications, Jul. 23, 2010.
Tatjana Schutze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Jiaqi Huang et al., "Rapid Screening of Complex DNA Samples by Single-Molecule Amplification and Sequencing," PLoS ONE, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 7381, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite TM Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.
Philippe Bécamel, Authorized Officer, The International Bureau of WIPO, "International Preliminary Report on Patentability" in connection with related PCT Patent App. No. PCT/US2011/026901, 15 pgs., Sep. 4, 2012.
A. Scherer, California Institute of Technology, "Polymerase Chain Reactors" PowerPoint presentation, 24 pgs., date unknown.
Eschenback Optik GMBH, Optics for Concentrated Photovoltaics (CPV), 1 pg., date unknown.
Abe (1999) Current opinion in colloid and interface science, vol. 4, pp. 354-356.
Japanese Patent Office, "Notice of Reasons for Rejection" in connection with related Japanese Patent Application No. 2012-556218, dated Apr. 6, 2015, 4 pgs.
European Patent Office, "Communication Pursuant to Article 94(3)EPC" Examination Report in connection with related European Patent Appln No. 11751314.3, dated Sep. 3, 2014, 6 pages.
European Patent Office, "European Extended Search Report" in connection with related European Patent Appln No. 11751314.3, dated Jul. 30, 2013, 6 pages.
Alexandridis, Structural Polymorphism of Poly(ethylene oxide)-Poly(propylene oxide) Block Copolymers in Nonaqueous Polar Sovents, Macromolecules, vol. 31 (1998) 6935-6942.
Young, Lee W., Authorized officer, International Searching Authority, "International Search Report", PCT Application No. PCT/US2011/26901; dated May 6, 2010.

(56) References Cited

OTHER PUBLICATIONS

Young, Lee W., Authorized officer, International Searching Authority, Written Opinion of the International Searching Authority, PCT Application No. PCT/US 2011/26901, dated May 6, 2010.

Richard Williams et al., "Amplification of complex gene libraries by emulsion PCR", Nature Methods, published online Jun. 21, 2006, vol. 3, No. 7, pp. 545-550.

Linas Mazutis et al., "A fast and efficient microfluidic system for highly selective one-to-one droplet fusion", The Royal Society of Chemistry 2009, Lab on a Chip, published Jun. 12, 2009, vol. 9, pp. 2665-2672.

"Office Action Summary" in connection with corresponding U.S. Appl. No. 12/976,816, dated May 25, 2012, 46 pgs.

* cited by examiner

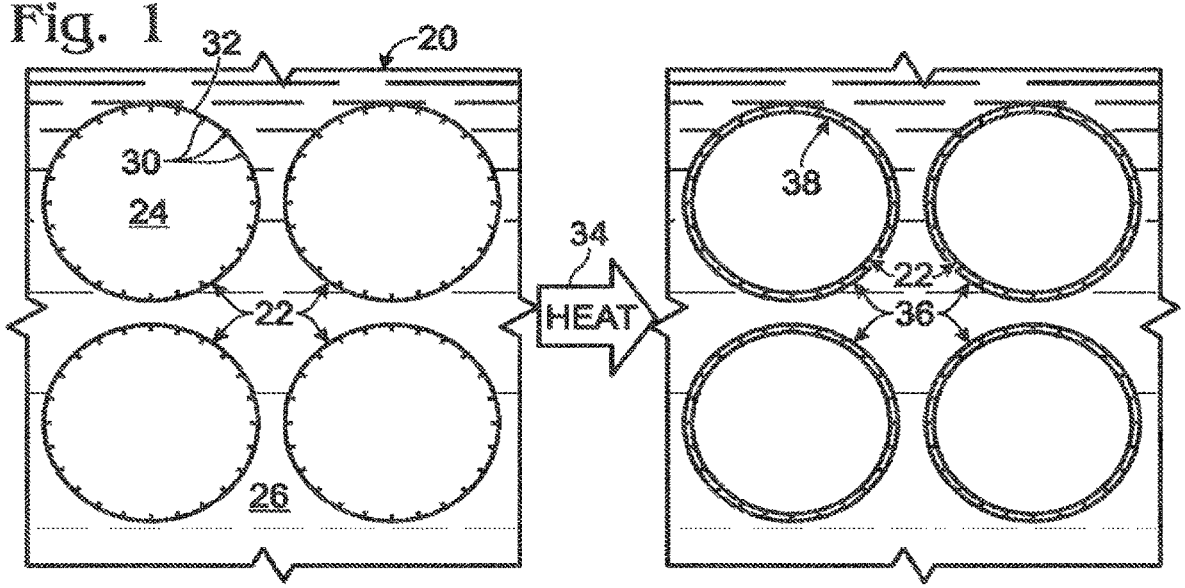
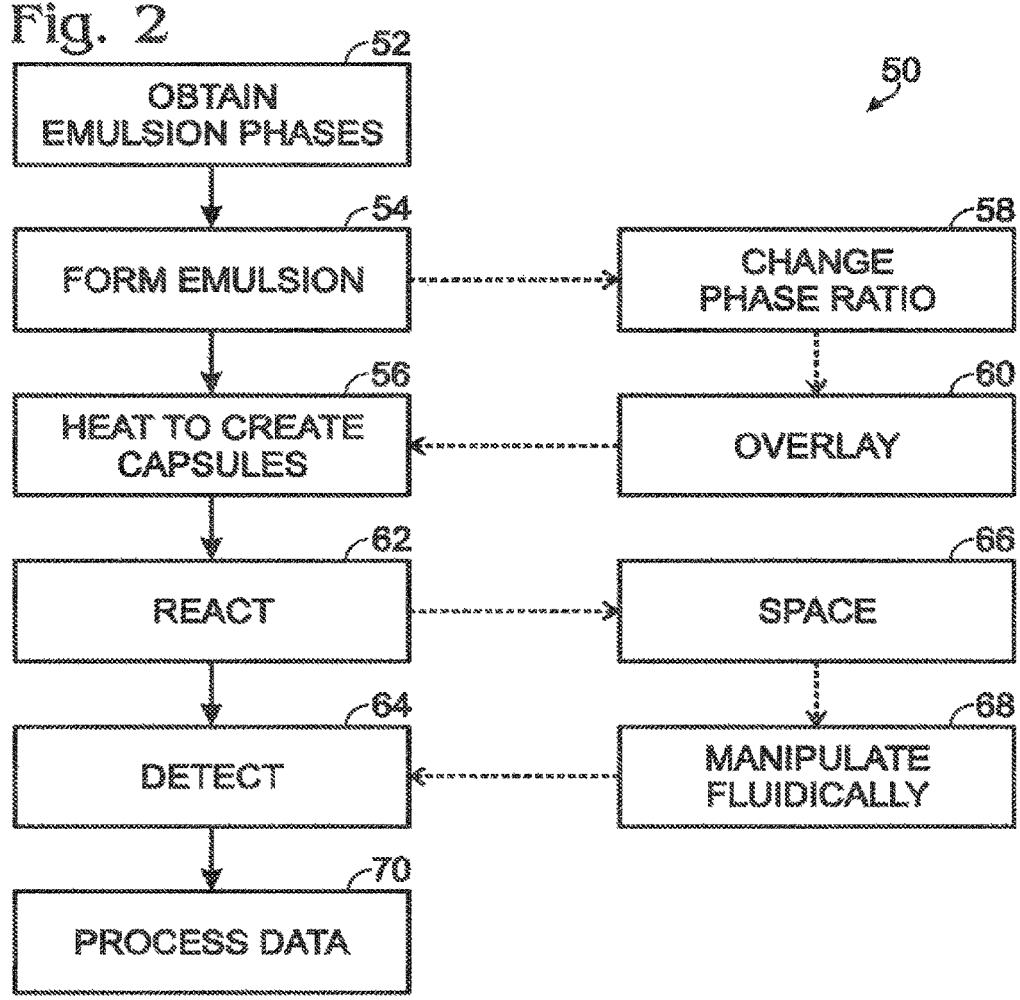

EMULSION CHEMISTRY FOR ENCAPSULATED DROPLETS

CROSS-REFERENCES TO PRIORITY APPLICATIONS

This application is a continuation of U.S. patent application Ser. No. 15/452,582 filed Mar. 7, 2017, which is a continuation of U.S. patent application Ser. No. 12/976,827, filed Dec. 22, 2010, which is based upon and claims the benefit under 35 U.S.C. § 119(e) of U.S. Provisional Patent Application Ser. No. 61/309,845, filed Mar. 2, 2010; U.S. Provisional Patent Application Ser. No. 61/341,218, filed Mar. 25, 2010; U.S. Provisional Patent Application Ser. No. 61/317,635, filed Mar. 25, 2010; U.S. Provisional Patent Application Ser. No. 61/380,981, filed Sep. 8, 2010; U.S. Provisional Patent Application Ser. No. 61/409,106, filed Nov. 1, 2010; U.S. Provisional Patent Application Ser. No. 61/409,473, filed Nov. 2, 2010; U.S. Provisional Patent Application Ser. No. 61/410,769, filed Nov. 5, 2010; and U.S. Provisional Patent Application Ser. No. 61/417,241, filed Nov. 25, 2010; each of which is incorporated herein by reference in its entirety for all purposes.

CROSS-REFERENCES TO ADDITIONAL MATERIALS

This application incorporates by reference in their entirety for all purposes the following materials: U.S. Pat. No. 7,041,481, issued May 9, 2006; U.S. patent application Ser. No. 12/862,542, filed Aug. 24, 2010, now U.S. Pat. No. 9,194,861; U.S. Patent Application Publication No. 2010/0173394 A1, published Jul. 8, 2010 (application Ser. No. 12/586,626), now U.S. Pat. No. 9,156,010; and Joseph R. Lakowicz, PRINCIPLES OF FLUORESCENCE SPECTROSCOPY ($2^{nd}$ Ed. 1999).

INTRODUCTION

Many biomedical applications rely on high-throughput assays of samples combined with reagents. For example, in research and clinical applications, high-throughput genetic tests using target-specific reagents can provide accurate and precise quantification of nucleic acids for drug discovery, biomarker discovery, and clinical diagnostics, among others.

The trend is toward reduced volumes and detection of more targets. However, mixing smaller volumes can require more complex instrumentation, which increases cost. Also, assays performed in smaller volumes may tend be less accurate. Accordingly, improved technology is needed to permit testing more combinations of samples and reagents, at a higher speed, a lower cost, with reduced instrument complexity, and/or with greater accuracy and precision, among others.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Splitting a sample into droplets offers numerous advantages. Small reaction volumes (picoliters to nanoliters) can be utilized, allowing earlier detection by increasing reaction rates and forming more concentrated products. Also, a much greater number of independent measurements (thousands to millions) can be made on the sample, when compared to conventional bulk volume reactions performed on a microliter scale. Thus, the sample can be analyzed more accurately (i.e., more repetitions of the same test) and in greater depth (i.e., a greater number of different tests). In addition, small reaction volumes use less reagent, thereby lowering the cost per test of consumables. Furthermore, microfluidic technology can provide control over processes used for generation, mixing, incubation, splitting, sorting, and detection of droplets, to attain repeatable droplet-based measurements.

Aqueous droplets can be suspended in oil to create a water-in-oil emulsion (W/O). The emulsion can be stabilized with a surfactant to reduce coalescence of droplets during heating, cooling, and transport, thereby enabling thermal cycling to be performed. Accordingly, emulsions have been used to perform single-copy amplification of nucleic acid target molecules in droplets using the polymerase chain reaction (PCR).

Compartmentalization of single molecules of a nucleic acid target in droplets of an emulsion alleviates problems encountered in amplification of larger sample volumes. In particular, droplets can promote more efficient and uniform amplification of targets from samples containing complex heterogeneous nucleic acid populations, because sample complexity in each droplet is reduced. The impact of factors that lead to biasing in bulk amplification, such as amplification efficiency, G+C content, and amplicon annealing, can be minimized by droplet compartmentalization. Unbiased amplification can be critical in detection of rare species, such as pathogens or cancer cells, the presence of which could be masked by a high concentration of background species in complex clinical samples.

The accuracy and reproducibility of droplet-based assays often relies on droplets having a uniform, stable size. However, maintaining the integrity of droplets can present a challenge. Manipulation and processing of droplets can cause the droplets to break, coalesce, or both, which can change an emulsion with a uniform size of droplets (a monodisperse emulsion) to one with a wide range of droplets (a polydisperse emulsion). For example, emulsions can become unstable as the packing density of droplets is increased, because droplet proximity enables coalescence. This instability limits the ability to store droplets. Also, the tendency of droplets to coalesce at a high packing density restricts the options for batch processing of droplets in a bulk phase. The tendency of droplets both to coalesce and break is exacerbated by higher temperatures and particularly the repetitive cycles of heating and cooling that are utilized for PCR amplification of a nucleic acid target in droplets. In addition, fluidic manipulation can damage droplets. Droplets may be induced to coalesce by an electric field ("electro-coalescence"), which can be created by a static charge on a surface. Accordingly, droplets may be induced to coalesce during fluidic manipulation, such as in a flow channel, or during aspiration into or dispensing from a pipet tip, among others. Furthermore, emulsion droplets tend to be susceptible to breakage when subjected to shear, such as when flowing in a channel and/or when there is a sudden change in direction of flow. For quantitative assays, droplet aggregation, coalescence, and breakage can all introduce large errors to make the assays inaccurate and unreliable.

New systems are needed to make and use emulsions having droplets that are more stable to storage, thermal cycling, a high packing density, and/or fluidic manipulation.

SUMMARY

The present disclosure provides a system, including methods, apparatus, compositions, and kits, for making and using a stabilized emulsion. A method of generating a stabilized emulsion is provided. In the method, an aqueous phase may be provided. The aqueous phase may include an effective concentration of one or more skin-forming proteins. An emulsion may be formed. The emulsion may include droplets of a dispersed phase disposed in a continuous phase, with the aqueous phase being the continuous phase or the dispersed phase. The emulsion may be heated to create an interfacial skin between each droplet and the continuous phase, to transform the droplets into capsules.

BRIEF DESCRIPTION OF THE DRAWINGS

FIG. 1 is a schematic diagram illustrating exemplary formation of skins to encapsulate droplets of an emulsion, in accordance with aspects of the present disclosure.

FIG. 2 is a flowchart illustrating an exemplary method of forming a stabilized emulsion including droplets encapsulated by a skin and of using the encapsulated droplets to perform an assay, in accordance with aspects of the present disclosure.

DETAILED DESCRIPTION

Figure 3:
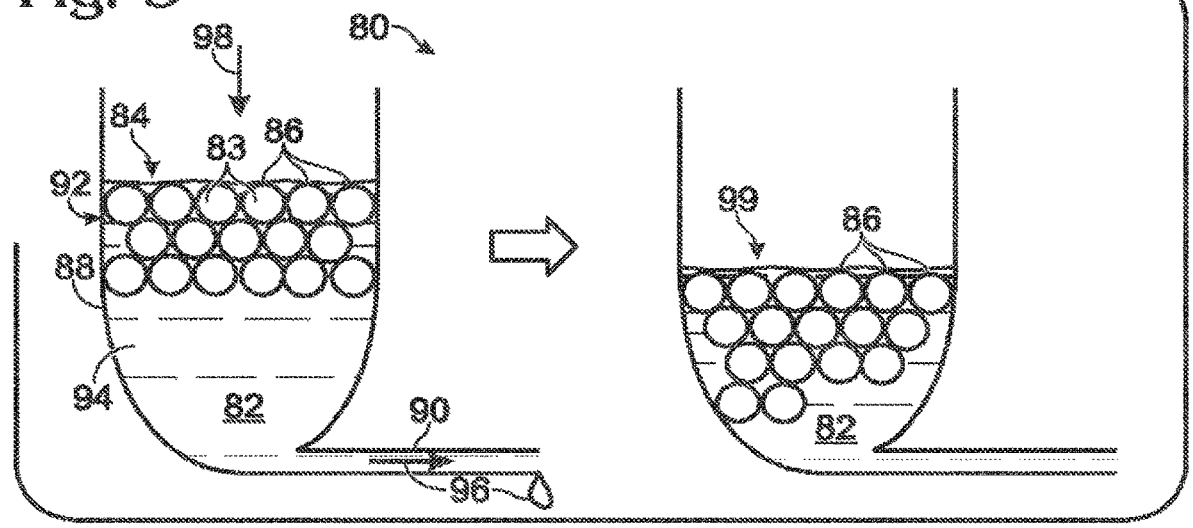
FIG. 3 is a schematic illustration of an exemplary approach of removing a continuous phase selectively from an emulsion to increase the volume fraction of the dispersed phase, in accordance with aspects of the present disclosure.

The present disclosure provides an emulsion chemistry for a system, including methods, apparatus, compositions, and kits, for making and using droplets encapsulated by a skin. The skin-encapsulated droplets, or capsules, may be resistant to coalescence, aggregation, and breakage over a wide range of thermal and mechanical processing conditions. The capsules may be used to provide more stable encapsulation of samples or analytes, such as nucleic acids, proteins, cells, or the like, and may be used in a wide range of biomedical applications, such as assays, drug and/or vaccine delivery, housing biomolecular libraries, clinical imaging applications, and the like.

A method of generating a stabilized emulsion is provided. In the method, an aqueous phase may be provided, which includes an effective concentration of one or more skin-forming proteins. An emulsion also may be formed, with the emulsion including droplets of the aqueous phase disposed in a nonaqueous continuous phase. Alternatively, an emulsion may be formed with the emulsion including droplets of the nonaqueous phase disposed in an aqueous continuous phase. Accordingly, the emulsion may be an oil-in-water emulsion or a water-in-oil emulsion, among others. The emulsion may be heated to create an interfacial skin between each droplet and the continuous phase, to transform the droplets into capsules.

The aqueous phase provided may include the skin-forming proteins and at least one surfactant. The protein(s) may be present at a concentration of at least about 0.01%, 0.03%, or 0.1%, by weight, among others. In some cases, although the skin may form at a concentration of 0.01%, the skin may not be amplification-compatible unless formed at a higher concentration of skin-forming protein, such as at least about 0.03%. An amplification-compatible skin (which may be termed a PCR-compatible skin) permits amplification, such as by PCR, of a nucleic acid target. In other words, the skin does not inhibit amplification enough, if at all, to prevent the amplification reaction from occurring efficiently. In any event, the skin-forming protein(s) may be present at a concentration of about 0.01% to 10%, 0.01% to 3%, 0.01% to 1%, 0.03% to 10%, 0.03% to 3%, 0.03% to 1%, 0.05% to 2%, or 0.1% to 1% by weight, among others. The protein(s) may, for example, be selected from the group consisting of albumin (e.g., bovine serum albumin (BSA)), gelatin, globulin (e.g., beta-lactoglobulin), and casein, among others. The skin may be a proteinaceous (protein-containing) skin composed at least substantially of the skin-forming protein(s). Alternatively, or in addition, the skin may not form substantially when the protein(s) is omitted from the aqueous phase (everything else being equal). In other words, the protein(s) may be required for skin formation. The surfactant may, for example, include a block copolymer of polypropylene oxide and polyethylene oxide.

A nonaqueous phase may be provided and the emulsion may be formed with the nonaqueous phase as a continuous phase (or a dispersed phase). The nonaqueous phase may be an organic or oil phase including at least one fluorinated oil and a fluorinated surfactant (e.g., a fluorinated polyether and/or a fluorinated alcohol, among others).

A method of emulsion preparation is provided. In the method, aqueous droplets may be generated in a continuous phase that includes a fluorinated oil and a fluorinated surfactant. The droplets may be transformed to capsules each including an aqueous phase encapsulated by a proteinaceous, interfacial skin. A spacing fluid may be added to the continuous phase, with the spacing fluid being miscible with the continuous phase and having a different composition than the continuous phase.

A method of performing an assay is provided. In the method, an aqueous phase including a sample and an effective concentration of one or more skin-forming proteins may be provided. An emulsion also may be formed, with the emulsion including droplets of the aqueous phase disposed in a nonaqueous continuous phase. The emulsion may be heated (e.g., to a temperature above about 50° C., 55° C. or 90° C.), to create an interfacial skin between each droplet and the continuous phase, to transform the droplets into capsules. In some embodiments, the emulsion may be thermally cycled to promote amplification of one or more nucleic acid targets in the capsules. Assay data related to the sample may be collected from the capsules. The assay data may be processed to determine an aspect of the sample, such as a concentration of an analyte (e.g., one or more nucleic acid targets) in the sample.

Another method of performing an assay is provided. An aqueous phase may be provided that includes an effective concentration of one or more skin-forming proteins. An oil phase may be provided that includes at least one fluorinated oil and a fluorinated surfactant. An emulsion may be formed that includes droplets of the aqueous phase disposed in the oil phase, or vice versa. The droplets may be transformed into capsules by creating an interfacial skin between each droplet and the oil phase (or aqueous phase). The capsules may be thermally cycled to amplify a nucleic acid target in the capsules. Amplification data may be collected from the capsules.

A composition for generating a stabilized emulsion is provided. The composition may comprise a continuous phase including a fluorinated oil and at least one fluorinated surfactant. The composition also may comprise a plurality of aqueous droplets disposed in the continuous phase and including an effective concentration of a skin-forming protein. Heating the emulsion above a threshold temperature may create an interfacial skin between each droplet and the continuous phase, to transform the droplets into capsules.

A stabilized emulsion is provided. The emulsion may comprise a continuous phase including a fluorinated oil and at least one fluorinated surfactant. The emulsion also may comprise a plurality of capsules disposed in the continuous phase, with each capsule including a proteinaceous, interfacial skin encapsulating an aqueous phase.

An assay kit is provided. The assay kit may include an aqueous phase including an effective concentration of one or more skin-forming proteins and a nonaqueous continuous phase including a fluorinated oil and at least one fluorinated surfactant. The assay kit also may include a droplet generator capable of forming an emulsion including droplets of the aqueous phase disposed in the nonaqueous continuous phase. Heating the emulsion above a threshold temperature may create an interfacial skin between each droplet and the continuous phase, to transform the droplets into capsules.

The present disclosure provides methods for preparing capsules of aqueous phases, including aqueous phases suitable for sample analysis, and the capsules prepared thereby. These capsules may be particularly useful for small volume PCR analysis. The disclosed methods may involve separating samples, such as clinical or environmental samples, into many small capsules containing an analyte of interest. For example, each capsule may contain less than about one copy of a nucleic acid target (DNA or RNA). The nucleic acid or other analyte in these capsules may be reacted, detected, and/or analyzed, using any suitable technique(s). The preparation, reaction, detection, and/or analysis of the disclosed capsules may be performed in series and/or in parallel, alone, or in combination with other processes. The present disclosure emphasizes, but is not limited to, capsules suitable for performing capsule-based amplification assays.

Further aspects of the emulsion chemistry and a system that uses the emulsion chemistry are described in the following sections, including: (I) definitions, (II) system overview, (III) aqueous phase, (IV) nonaqueous phase, (V) formation of emulsions, (VI) droplet transformation, (VII) capsules, (VIII) spacing fluid, (IX) capsule and data processing, and (X) examples.

I. DEFINITIONS

Technical terms used in this disclosure have the meanings that are commonly recognized by those skilled in the art. However, the following terms may have additional meanings, as described below.

Assay—a procedure that incorporates one or more reactions, and that is used to characterize a sample of interest. Such characterization may be obtained by virtue of one or more signal(s), value(s), data, and/or result(s) obtained from the procedure(s) and/or reaction(s). An assay may be performed using at least one "assay mixture" which is a composition from which one or more test signals are detected, before, during, and/or after processing of the composition to permit a reaction, if any, to occur. A test or assay may determine a presence (e.g., concentration) or activity, among others, of one or more analytes in a sample.

Reaction—a chemical reaction, a binding interaction, a phenotypic change, or a combination thereof. An exemplary reaction is enzyme-catalyzed conversion of a substrate to a product and/or binding of a substrate or product to a binding partner.

Reagent—a compound, set of compounds, and/or composition that is combined with a sample in order to perform a particular test on the sample. A reagent may be a target-specific reagent, which is any reagent composition that confers specificity for detection of a particular target or analyte in a test. A reagent optionally may include a chemical reactant and/or a binding partner for the test. A reagent may, for example, include at least one nucleic acid, protein (e.g., an enzyme), cell, virus, organelle, macromolecular assembly, a potential drug, a lipid, a carbohydrate, an inorganic substance, or any combination thereof, among others. In exemplary embodiments, the reagent may be an amplification reagent, such as at least one primer or a pair of primers for amplification of a target, and/or at least one probe to provide an amplification signal.

Nucleic acid—a compound comprising a chain of nucleotide monomers. A nucleic acid may be single-stranded or double-stranded (i.e., base-paired with another nucleic acid), among others. The chain of a nucleic acid may be composed of any suitable number of monomers, such as at least about ten or one hundred, among others. Generally, the length of a nucleic acid chain corresponds to its source, with synthetic nucleic acids (e.g., nucleic acid reagents such as primers and probes) typically being shorter and biologically produced nucleic acids (e.g., nucleic acid analytes) typically being longer.

A nucleic acid can have a natural or artificial structure, or a combination thereof. Nucleic acids with a natural structure, namely, deoxyribonucleic acid (DNA) and ribonucleic acid (RNA), have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of adenine-thymine and guanine-cytosine base pairs with the other nucleic acid is termed "complementary."

Replication—a process forming a complementary copy of a nucleic acid or a segment thereof. The nucleic acid and/or segment replicated is a template (and/or a target) for replication.

Amplification—a process in which a copy number increases. Amplification may be a process in which replication occurs repeatedly over time to form multiple copies of a template. Amplification can produce an exponential or linear increase in the number of copies as amplification proceeds. Exemplary amplification strategies include polymerase chain reaction (PCR), loop-mediated isothermal amplification (LAMP), rolling circle replication (RCA), cascade-RCA, nucleic acid based amplification (NASBA), and the like. Also, amplification can utilize a linear or circular template. Amplification can be performed under any suitable temperature conditions, such as with thermal cycling or isothermally. Furthermore, amplification can be performed, or tested for its occurrence, in an amplification mixture, which is any composition capable of amplifying a nucleic acid target, if any, in the mixture. An amplification mixture can include any combination of at least one primer, at least one probe, at least one replication enzyme (e.g., at least one polymerase, such as at least one DNA and/or RNA polymerase), deoxynucleotide (and/or nucleotide) triphosphates (dNTPs and/or NTPs), a magnesium salt, or any combination thereof, among others. The amplification mixture may include at least one magnesium-dependent enzyme.

PCR—amplification that relies on repeated cycles of heating and cooling (i.e., thermal cycling) to achieve successive rounds of replication. PCR can be performed by thermal cycling between two or more temperature setpoints, such as a higher denaturation temperature and a lower annealing/extension temperature, or among three or more temperature setpoints, such as a higher denaturation temperature, a lower annealing temperature, and an intermediate extension temperature, among others. PCR can be performed with a thermostable polymerase, such as Taq DNA polymerase. PCR generally produces an exponential increase in the amount of a product amplicon over successive cycles.

RT-PCR (reverse transcription-PCR)—PCR utilizing a complementary DNA template produced by reverse transcription of RNA. RT-PCR permits analysis of an RNA sample by (1) forming complementary DNA copies of RNA, such as with a reverse transcriptase enzyme, and (2) PCR amplification using the complementary DNA as a template.

Amplicon—a product of an amplification reaction. An amplicon can be single-stranded or double-stranded, or a combination thereof. An amplicon corresponds to any suitable segment or the entire length of a nucleic acid target.

Primer—a nucleic acid capable of, and/or used for, priming replication of a nucleic acid template. Thus, a primer is a shorter nucleic acid that is complementary to a longer template. During replication, the primer is extended, based on the template sequence, to produce a longer nucleic acid that is a complementary copy of the template. A primer may be DNA, RNA, or an analog thereof (i.e., an artificial nucleic acid), and may have any suitable length, such as at least about 10, 15, or 20 nucleotides. Exemplary primers are synthesized chemically. Primers may be supplied as a pair of primers for amplification of a nucleic acid target. The pair of primers may be a sense primer and an antisense primer that collectively define the opposing ends (and thus the size) of a resulting amplicon. In some embodiments, at least one primer may be described as a molecular inversion probe (MIP).

Probe—a nucleic acid connected to a label. A probe may be a sequence-specific binding partner for a nucleic acid target and/or amplicon. An exemplary probe includes one or more nucleic acids connected to a pair of dyes that collectively exhibit fluorescence resonance energy transfer (FRET) when proximate one another. The pair of dyes may respectively provide first and second emitters or an emitter (a reporter) and a quencher. Fluorescence emission from the pair of dyes changes when the dyes are separated from one another, such as by cleavage of the probe (e.g., a Taqman probe) during primer extension, or when the probe (e.g., a molecular beacon probe) binds to an amplicon. A "molecular inversion probe" may or may not be connected to a label.

Label—an identifying and/or distinguishing marker or identifier connected to or incorporated into any entity, such as a molecule, molecular complex, compound, biological particle, or droplet. The label may be described as labeling the particular entity to produce a labeled entity. A label may, for example, be a dye that renders an entity optically detectable or at least more optically detectable. Exemplary dyes used for labeling are fluorescent dyes (fluorophores) and fluorescence quenchers.

Binding partner—a member of a pair of members that bind to one another. Each member may be an atom, molecule, molecular complex, compound, and/or biological particle (a cell, virus, organelle, or the like), among others. Binding partners may bind specifically to one another. Specific binding can be characterized by a dissociation constant of less than about $10^{-4}$, $10^{-6}$, $10^{-8}$, or $10^{-10}$ M. Exemplary specific binding partners include biotin and avidin/streptavidin, a sense nucleic acid and a complementary antisense nucleic acid, a primer and its target, an antibody and a corresponding antigen, a receptor and its ligand, a nucleic acid and a protein that recognizes a sequence motif present in the nucleic acid, and the like.

Fluorinated—including fluorine, typically substituted for hydrogen. Any of the fluorinated compounds disclosed herein may be polyfluorinated, meaning that such compounds each include many fluorines, such as more than five or ten fluorines, among others. Any of the fluorinated compounds disclosed herein also or alternatively may be perfluorinated, meaning that most or all hydrogens have been replaced with fluorine.

II. SYSTEM OVERVIEW

The system of the present disclosure exploits an emulsion chemistry that enables formation of skins to encapsulate and stabilize droplets of an emulsion. The droplets may be stabilized against thermal and mechanical stress, among others, to reduce breakage and coalescence.

FIG. 1 shows a schematic diagram illustrating exemplary formation of skins around droplets. An emulsion 20 is obtained that includes droplets 22 of an aqueous dispersed phase 24 disposed in a nonaqueous continuous phase 26. The droplets may be spaced from one another by any suitable average distance to generate any suitable packing density. For example, the droplets may be packed closely together, such as with a packed arrangement having a high packing density. A high packing density is a packed arrangement of droplets in which the collective droplet volume of the packed arrangement (i.e., the dispersed phase volume) is at least about as great as the interstitial volume of the packed arrangement (i.e., the volume of the continuous phase (or portion thereof) that is disposed among droplets within the packed arrangement). In other words, in a high packing density, the dispersed phase volume is at least about 50% of the sum of the dispersed phase volume and the interstitial volume. A packed arrangement may be produced by a density difference between the dispersed phase and the continuous phase that causes the droplets to be buoyant or to sink in the continuous phase, in response to gravity and/or application of a centripetal force. If the droplets are monodisperse, the high packing density may be provided by a substantially regular arrangement (a lattice arrangement) of the droplets.

The aqueous phase may be a skin-forming mixture and may include one or more skin-forming materials 30, such as at least one skin-forming protein. For example, at least one skin-forming material may be localized interfacially, that is, near or at an interface or droplet boundary 32 created between each droplet 22 and continuous phase 26.

The droplets may be transformed to capsules. For example, the droplets, the emulsion, and/or the continuous phase may be heated, indicated at 34, to form capsules 36. Each capsule includes an interfacial skin 38 formed near or at interface 32, to encapsulate an aqueous phase of each droplet 22. The capsules, relative to the progenitor droplets, may be more stable to various treatments. For example, the capsules may permit longer storage (such as at about 4° C. to 40° C.) without substantial loss of droplet integrity. Also, the capsules may be more resistant to coalescence and breakage when heated and/or thermocycled to promote reaction and/or amplification. Further, the capsules may be more resistant to breakage and/or coalescence produced by an electric field or mechanical stress (such as fluidic manipulations). Capsules (and/or an emulsion) resistant to coalescence exhibit less than about 5%, 2%, or 1% of the capsules coalescing to form larger capsules/droplets in a given time period, at a given temperature, and with a given capsule packing density. In some cases, the capsules may be resistant to coalescence when incubated at 70° C., 80° C., or 90° C., for at least 1, 2, 5, or 10 minutes, with the capsules at a high packing density. Alternatively, or in addition, the capsules may be resistant to coalescence when stored at 4° C., 20° C., or 37° C. for at least one week or one month, with the capsules at a high packing density. Furthermore, the capsules may be more resistant to coalescence when subjected to an electric field (e.g., from a static charge), and more resistant to coalescence and breakage when manipulated fluidically, such as at relatively high flow rates and/or with changes in flow direction or pressure. Moreover, the skin may form a biocompatible interface (e.g., in place of an oil-water interface) that reduces adsorption of analytes and/or reagents to the interface from within the droplets.

FIG. 2 illustrates an exemplary method 50 of forming droplets encapsulated by a skin and of using the encapsulated droplets to perform an assay. The method steps presented here may be performed in any suitable order, in any suitable combination, and may be combined with any other method steps or features described elsewhere in the present disclosure or in the documents listed above under Cross-References, which are incorporated herein by reference, particularly U.S. Provisional Patent Application Ser. No. 61/309,845, filed Mar. 2, 2010; U.S. Provisional Patent Application Ser. No. 61/317,635, filed Mar. 25, 2010; U.S. Provisional Patent Application Ser. No. 61/380,981, filed Sep. 8, 2010; U.S. Provisional Patent Application Ser. No. 61/409,106, filed Nov. 1, 2010; U.S. Provisional Patent Application Ser. No. 61/409,473, filed Nov. 2, 2010; U.S. Provisional Patent Application Ser. No. 61/410,769, filed Nov. 5, 2010; U.S. Provisional Patent Application Ser. No. 61/417,241, filed Nov. 25, 2010; and U.S. Patent Application Publication No. 2010/0173394 A1, published Jul. 8, 2010.

Phases for an emulsion may be provided, indicated at 52. The phases generally include an aqueous phase and a nonaqueous phase that are immiscible with one another. The phases may be formulated to promote skin formation when the emulsion is heated. For example, the aqueous phase may include one or more skin-forming components. A skin-forming component is any component of a skin-forming mixture that is necessary for skin formation: omitting only the skin-forming component from the mixture causes the skin not to form, everything else being equal. An exemplary skin-forming component is a skin-forming protein. The skin-forming protein (or proteins) may be present at an effective concentration, which is a concentration sufficient to form a detectable skin when the droplets are appropriately heated or treated otherwise to promote skin formation. The aqueous phase also may include a sample and may be configured to perform a reaction involving the sample. In exemplary embodiments, the aqueous phase provides a reaction mixture for amplification of at least one nucleic acid target.

The sample may include nucleic acid. The nucleic acid may, for example, be DNA (e.g., genomic DNA), RNA (e.g., messenger RNA and/or genomic RNA), and/or cDNA (DNA produced by reverse transcription of RNA), among others.

An emulsion may be formed, indicated at 54. The emulsion may include droplets of the aqueous phase disposed in a continuous phase provided by the nonaqueous phase. The nonaqueous phase may include oil and/or may be formed predominantly by oil, such that the emulsion is a water-in-oil emulsion. In some embodiments, each droplet may be separated from the nonaqueous phase by an interfacial layer that is composed substantially of one or more skin-forming components.

The emulsion may be heated to create capsules in which droplets are encapsulated by a skin, indicated at 56. Heating may be performed at a temperature and for a time period sufficient to form the skin, such as to convert an interfacial layer composed of one or more skin-forming components to an interfacial skin. The emulsion may be held by a container (e.g., a vial, a chamber, a well of a multi-well plate, etc.) while heated (and/or reacted, see below), or may be disposed in and/or flowing along a channel.

In some embodiments, the emulsion may be heated while held in a container (e.g., a well of a multi-well plate) that is sealed with a pierce-able sealing member (e.g., a foil, a film, or the like). The sealing member may be conformable. The sealing member may be pierced with a tip of a fluid transfer device, such as a pipet tip, a needle, or the like, to permit removal of the emulsion from the container and/or addition of fluid (and/or reagent) to the container. Removal of at least a portion of the emulsion from the container may be performed after skin formation and/or after reaction of the capsules (e.g., amplification of a nucleic acid target in the capsules), among others.

The capsules may be used immediately or may be stored for any suitable time period before use (e.g., in some cases, stored for at least one day, week, or month, among others). The resulting capsules generally are more stable than the droplets. For example, the capsules may be more stable to shear, and may be stored for extended periods without degradation. The stability of the capsules enables bulk processing and manipulation that can substantially damage droplets not encapsulated by skin.

In some embodiments, the droplets may not be encapsulated by a skin. Accordingly, any of the steps described in this section, elsewhere in the present disclosure, or in the documents listed above under Cross-References, which are incorporated herein by reference, may be performed with droplets instead or in addition to capsules.

The phase ratio of the emulsion may be changed, indicated at 58, before heating to create capsules (56). Changing the phase ratio is optional and includes any procedure that substantially increases and/or decreases the volume fraction of the aqueous phase in the emulsion. For example, the volume fraction of the aqueous phase may be increased by selectively removing a portion of the continuous phase (relative to the aqueous phase) from the emulsion. In some cases, excess continuous phase may be removed to produce a high volume fraction of the aqueous phase, such as at least about 50%, among others, in the emulsion. To permit selective removal of droplets or the continuous phase, the emulsion may be formulated with the aqueous and nonaqueous phases having different densities, such that the droplets tend to sink or float in the emulsion, to promote sedimentation or creaming, respectively. In exemplary embodiments, the droplets are buoyant (or sink) in the continuous phase, permitting the emulsion to be concentrated by selectively removing droplets from a top portion (or bottom portion) of the emulsion and/or selectively removing the continuous phase from a bottom portion (or top portion) of the emulsion. Further aspects of changing the phase ratio of an emulsion are described below in Example 1 of Section X.

In some embodiments, removing a portion of the continuous phase may improve stability of droplets prior to and/or after the transformation to capsules. For some cases, such as when the concentration of at least one ionic surfactant in the oil phase (continuous phase) is above the CMC (critical micelle concentration), there may be an excess of ionic surfactant that exists in micelles, and these micelles may compete with the droplets or capsules through a thermodynamic driving force that draws water out of the droplets or capsules, causing them to shrink or even tear (in the case of the skin-bearing capsules). Accordingly, any approach that reduces the amount of excess ionic micelles in the continuous phase may improve droplet or capsule stability. Some examples of steps that can be taken include (1) removal of at least a portion of excess continuous phase (in other words, removal of some micelles) prior to transformation of droplets to capsules and/or (2) use of reduced surfactant concentration in (a) the continuous phase at the time of emulsion formation (provided a sufficient amount of surfactant is present to generate and sustain intact droplets), and/or (b) the continuous phase for any capsule spacing or transport fluids (described in more detail elsewhere in the present disclosure).

Another pre-transformation step that may be effective to reduce loss of water from droplets/capsules to the continuous phase is to "pre-saturate" or "pre-hydrate" the continuous phase with water, rather than or in addition to removing excess continuous phase to reduce the number of micelles. The continuous phase may be exposed to water before emulsion formation to achieve pre-hydration. For example, the continuous phase may be overlaid or otherwise disposed in contact with a volume of water or an aqueous, pre-hydration solution that more closely resembles (ionic, osmotic balance) the aqueous solution that will be disposed in the droplets when they are subsequently formed with the pre-hydrated continuous phase. The pre-hydration solution can, for example, be the buffered base for the reaction mixture within the droplets, generally excluding any nucleic acids or proteins/enzymes. The skin-forming material and any aqueous phase surfactants also may be excluded from the pre-hydration solution in some cases.

The emulsion optionally may be overlaid, indicated at 60. In some embodiments, where the droplets are buoyant compared to the continuous phase, an overlay may be useful to protect droplets from breakage or other degradation during exposure to air and/or other interfaces (e.g., the air-emulsion interface during a heating step to form capsules). An overlay also may be useful where the droplets sink compared to the interface, although continuous phase above the droplets may render an overlay unnecessary. In any event, an overlay may be placed onto the emulsion to cover a top surface of the emulsion, before (or after) the emulsion is heated to create capsules (56). The overlay contacts the emulsion and forms a layer that generally remains above the emulsion. Stated differently, the overlay may completely cover an air-exposed, top surface of the emulsion, to replace an emulsion-air interface with an emulsion-overlay interface, thereby reducing exposure of the emulsion to air. The overlay may reduce evaporation of a component(s) from either or both phases of the emulsion, such as evaporation of oil and water from the continuous and aqueous phases, respectively. In any event, the overlay may reduce droplet damage (e.g., breakage) that can occur before capsule formation with some formulations, as the emulsion is being heated, and/or capsule damage (e.g., desiccation/shrinkage) that can occur near an emulsion-air interface at relatively higher temperatures, such as during thermal cycling for PCR amplification.

The overlay may be fluid or solid when applied, and, if fluid when applied, may remain fluid or may solidify. The overlay (or a continuous phase thereof) may have a lower density than the continuous phase of the underlying emulsion, such that the overlay floats on the primary emulsion. A fluid overlay may have any suitable composition. For example, the fluid overlay may be an overlay emulsion (containing droplets and/or capsules) or an overlay phase. Further aspects of fluid overlays are described in Example 2 of Section X.

The emulsion may be reacted, indicated at 62. Generally, reaction of the emulsion involves treating the emulsion to promote individual reactions in capsules of the emulsion. For example, the emulsion may be heated and/or thermally cycled to promote amplification of a nucleic acid target in the capsules. Accordingly, heating may be part of a thermal cycling process or may be a pre-incubation (e.g., reverse transcription, uracil removal, endo- or exonuclease digestion, etc.) prior to a thermal cycling process. The pre-incubation step or first incubation step in an RT-PCR or PCR protocol may be used to transform droplets to capsules, to form the interfacial skin at a high packing density, at a lower packing density, or even with the droplets not packed (such as spaced in fluid under flow but exposed to heating), in order to further resist coalescence in subsequent manipulations of the capsules. This may be particularly useful where subsequent manipulations involve a high packing density of the capsules.

The droplets may be reacted in parallel, such as in a batch reaction performed in a container. If reacted in a batch reaction, the capsules may be at a high packing density. Alternatively, the droplets may be reacted in parallel or serially as the droplets flow along a channel of a continuous flow reactor, and/or the droplets may be heated in batch (e.g., at a high packing density) to form the skin, and then flowed through the continuous flow reactor (e.g., see U.S. Patent Application Publication No. 2010/0173394 A1, published Jul. 8, 2010, which is incorporated herein by reference), among others.

Signals may be detected from capsules of the emulsion, indicated at 64. Stated differently, assay data related to a sample in the aqueous phase may be collected from the capsules. The data may relate to at least one reaction involving one or more analytes in the sample. In exemplary embodiments, the data relates to amplification of a nucleic acid target in the capsules.

The capsules of the emulsion optionally may be spaced from one another, indicated at 66. Spacing the capsules may be performed one or more times before and/or after reaction of the emulsion and before detection of signals from the capsules. Spacing the capsules generally includes any manipulation that increases the average or local spacing between capsules of the emulsion.

The capsule spacing may be increased to facilitate fluidic manipulation of capsules that are in a packed arrangement of high density after reaction in a container. The packed arrangement may be the result of creaming/sedimentation alone or in combination with changing the phase ratio (58), such as by removal of excess continuous phase from the emulsion. In some embodiments, the packed arrangement may form a substantial lattice of capsules and/or may dispose the capsules in a substantial crystalline state, if the capsules are monodisperse (and, optionally, if the aqueous fraction is high).

The use of a spacing fluid to facilitate spacing the capsules from one another may be based on the volume fraction of the aqueous phase. The emulsion may have a more fluid consistency if the aqueous phase fraction is lower, such as approximately equal to or less than the continuous phase fraction. In this case, the capsules may (or may not) be dispersed readily (i.e., spaced farther from one another) without addition of a spacing fluid, such as by agitation of the emulsion. Alternatively, the emulsion may have a less fluid or more "gel-like" consistency, if the aqueous phase fraction is higher, such as higher than the continuous phase fraction. In this case (and/or with the fluid-like emulsion), the capsules may be dispersed with the aid of a spacing fluid added to the emulsion. In any event, the capsules may be spaced to facilitate flow, such as flow into a conduit of a fluid transport device that picks up droplets from the container, for example, via a tip of the device disposed in the emulsion. In some cases, thermally cycling capsules makes them "sticky" and more difficult to disperse. Addition of a spacing fluid may facilitate dispersal of sticky capsules.

Capsules also or alternatively may be spaced farther from one another to enable detection of individual droplets. Accordingly, a spacing fluid may be added to droplets flowing in a channel to a detection region that is operatively disposed with respect to a detector. The spacing fluid may be described as a focusing fluid, and may singulate the droplets before they reach the detection region. The singulated droplets may travel serially through the detection region. Further aspects of spacing droplets upstream of a detection region are disclosed in the documents listed above under Cross-References listed above, which are incorporated herein by reference, particularly U.S. Provisional Patent Application Ser. No. 61/317,635, filed Mar. 25, 2010; U.S. Provisional Patent Application Ser. No. 61/409,106, filed Nov. 1, 2010; U.S. Provisional Patent Application Ser. No. 61/409,473, filed Nov. 2, 2010; U.S. Provisional Patent Application Ser. No. 61/410,769, filed Nov. 5, 2010; and U.S. Patent Application Publication No. 2010/0173394 A1, published Jul. 8, 2010.

The emulsion optionally may be manipulated fluidically, indicated at 68. If the phase ratio is changed (66), such as by selective removal of droplets/capsules or the continuous phase, fluidic manipulation may be performed before, during, and/or after this change.

Fluidic manipulation generally involves moving the emulsion or droplets/capsules thereof by fluid flow. For example, fluidic manipulation may include dispersing droplets/capsules disposed in a container, introducing droplets/capsules from the container into a flow stream, dispersing droplets/capsules in the flow stream (e.g., singulating the capsules), and/or driving flow of capsules to a detection region, where a detector may collect data from the capsules serially or in parallel (e.g., by imaging).

Collected data may be processed, indicated at 70. Data processing may include determining at least one aspect of one or more analytes of one or more samples included in the aqueous phase of the emulsion. The data processing may include subtracting background, normalizing capsule data based on capsule size, applying a threshold to capsule signals to distinguish positive from negative capsules for the assay, determining a concentration of an analyte (e.g., a nucleic acid target) in the sample (e.g., based on Poisson statistics), or any combination thereof, among others.

The capsules may be used to perform any suitable assay to measure any suitable characteristic of an analyte. In some embodiments, the analyte is nucleic acid and amplification data from individual capsules may be analyzed to determine whether or not amplification of one or more nucleic acid targets occurred in individual droplets, in a digital amplification assay. In other words, the amplification data may be processed to provide a digital description of the presence or absence of each target in each droplet analyzed. In any event, the amplification data may be processed to provide information about any suitable aspect of a sample, such as the presence or absence of at least one single nucleotide polymorphism, methylation of a target site, copy number variation of a target, a rare mutation/target (e.g., a mutation associated with cancer), fetal aneuploidy, a haplotype, and the like. Further aspects of assays that may be suitable are described in the documents listed above Cross-References, which are incorporated herein by reference, particularly U.S. Patent Application Publication No. 2010/0173394 A1, published Jul. 8, 2010; U.S. Provisional Patent Application Ser. No. 61/380,981, filed Sep. 8, 2010; U.S. Provisional Patent Application Ser. No. 61/409,106, filed Nov. 1, 2010; U.S. Provisional Patent Application Ser. No. 61/410,769, filed Nov. 5, 2010; and U.S. Provisional Patent Application Ser. No. 61/417,241, filed Nov. 25, 2010.

Further aspects of emulsions, emulsion phases, phase components, generating droplets/forming emulsions, reacting emulsions, detecting signals, fluidic manipulation, and data processing, among others, that may be suitable are described in the documents listed above Cross-References, which are incorporated herein by reference, particularly U.S. Provisional Patent Application Ser. No. 61/341,218, filed Mar. 25, 2010; U.S. Provisional Patent Application Ser. No. 61/317,635, filed Mar. 25, 2010; U.S. Provisional Patent Application Ser. No. 61/409,106, filed Nov. 1, 2010; U.S. Provisional Patent Application Ser. No. 61/409,473, filed Nov. 2, 2010; U.S. Provisional Patent Application Ser. No. 61/410,769, filed Nov. 5, 2010; U.S. Provisional Patent Application Ser. No. 61/417,241, filed Nov. 25, 2010; and U.S. Patent Application Publication No. 2010/0173394 A1, published Jul. 8, 2010.

III. AQUEOUS PHASE

The aqueous phase is substantially and/or predominantly water, but may incorporate a variety of additional components. The components may be soluble and/or miscible in water, such as one or more salts, buffering agents, reagents, samples of interest, analytes of interest, and/or whatever additional components may be necessary for a desired reaction(s) that may be intended to occur within a formed droplet or capsule. All such additional components may be selected to be compatible with the desired reaction or intended assay. Additionally, the aqueous phase may include one or more skin-forming components.

In some cases, the components may include droplets disposed in the aqueous phase, such as one more simple or compound droplets. For example, the aqueous phase may contain one or more oil droplets, which in turn may (or may not) contain one or more aqueous droplets, and so on. Accordingly, the skin may encapsulate aqueous droplets that fuse with one another within the skin, during and/or after skin formation. Further aspects of forming multiple emulsions and inducing droplet fusion within multiple emulsions are described in U.S. patent application Ser. No. 12/862,542, filed Aug. 24, 2010, which is incorporated herein by reference.

Salts and/or Buffers

Any suitable salt or combination of salts may be present in the aqueous phase. Each salt may or may not be a physiologically compatible salt. Exemplary salts for the aqueous phase include any one or combination of NaCl, KCl, $CaCl_2$, $MgCl_2$, and $MgSO_4$, among others.

Any suitable buffer(s) or buffering agent(s) may be present in the aqueous phase. The buffer or buffering agent may be configured to maintain the pH of the aqueous phase near or at any suitable pH, such as a pH near or at which a desired reaction or set of reactions occurs efficiently (e.g., near an optimum pH for an enzyme activity). In some cases, the pH may, for example, approximate a physiological pH, such as about 6.5 to 8.5, 7 to 8, or about 7.5 among others. In any event, a particular buffering agent may be selected that has a pKa relatively close to the desired pH to be maintained and that is compatible with the reaction(s) to be performed. For example, the buffering agent may be physiologically compatible. Exemplary buffering agents that may be suitable include Tris (2-Amino-2-hydroxymethyl-propane-1,3-diol), MES (2-(N-morpholino) ethanesulfonic acid), MOPS (3-morpholinopropane-1-sulfonic acid), HEPES (2-[4-(2-hydroxyethyl)piperazin-1-yl] ethanesulfonic acid), and the like.

Reagents

Where the aqueous phase includes one or more reagents, the reagent is understood to be a compound, set of compounds, and/or composition that is combined with a sample of interest in order to perform a particular test on the sample. A reagent may be a target-specific reagent, which is any reagent composition that confers specificity for reaction with or detection of a particular target or analyte in a test. A reagent optionally may include a chemical reactant and/or a binding partner for the test. A reagent may, for example, include at least one nucleic acid, protein (e.g., an enzyme), cell, virus, organelle, macromolecular assembly, a potential drug, a lipid, a carbohydrate, an inorganic substance, or any combination thereof, among others. In exemplary embodiments, the reagent may be an amplification reagent, such as a polymerase (e.g., a heat-stable polymerase that may or may not require a hot start to activate the polymerase), a reverse transcriptase, a ligase, an exonuclease, at least one primer or at least one set of primers for amplification of a target, at least one probe to provide an amplification signal for the amplified target, or any combination thereof, among others. In some cases, the aqueous phase and droplets/capsules may include a molecular inversion probe (MIP). Further aspects of molecular inversion probes and their use in droplet-/capsule-based assays are described in U.S. Provisional Patent Application Ser. No. 61/380,981, filed Sep. 8, 2010; and U.S. Provisional Patent Application Ser. No. 61/417,241, filed Nov. 25, 2010; each of which is incorporated herein by reference.

Samples

Where the aqueous phase includes a sample, the sample is understood to be a compound, composition, and/or mixture of interest, from any suitable source(s). A sample may be the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, partitioning, further processing, or any combination thereof, among others. Clinical samples may include blood, saliva, urine, stool, sputum, mucous, milk, a fluid aspirate, and/or tissue, among others. Environmental samples may include water, soil, and/or air, among others. Research samples may include cultured cells, primary cells, viruses, small organisms, tissue, a body fluid, or the like. Additional samples may include foodstuffs, weapons components, suspected contaminants, and so on.

Analytes

Where the aqueous phase includes an analyte of interest, the analyte is understood to be a component(s) or potential component(s) of a sample that is analyzed in a test. An analyte is a more specific subject of interest in a test for which the sample is a more general subject of interest. An analyte may, for example, be a nucleic acid, a protein, an enzyme, a cell, a virus, an organelle, a macromolecular assembly, a drug candidate (and/or potential drug), a lipid, a carbohydrate, an inorganic substance, or any combination thereof, among others. An analyte may be tested for its concentration, activity, and/or other characteristic in a sample. The concentration of an analyte may relate to an absolute or relative number, binary assessment (e.g., present or absent), or the like, of the analyte in a sample or in one or more partitions thereof.

Surfactants

A surfactant is a surface-active substance capable of reducing the surface tension of a liquid in which it is present. A surfactant, which also or alternatively may be described as a detergent and/or a wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. The aqueous phase would typically incorporate at least one hydrophilic surfactant. The aqueous phase may include at least one nonionic surfactant and/or ionic surfactant. In some embodiments, the aqueous phase may include a surfactant that is a block copolymer of polypropylene oxide and polyethylene oxide. More particularly, the surfactant may be a block copolymer of polypropylene oxide and polyethylene oxide sold under the trade names PLURONIC and TETRONIC (BASF). In some embodiments, the surfactant may be a nonionic block copolymer of polypropylene oxide and polyethylene oxide sold under the trade name PLURONIC F-68. In some embodiments, the surfactant of the aqueous phase may be a water-soluble and/or hydrophilic fluorosurfactant. Exemplary fluorosurfactants for the aqueous phase are sold under the trade name ZONYL (DuPont), such as ZONYL FSN fluorosurfactants. In some cases, the surfactant may include polysorbate 20 (sold under the trade name TWEEN-20 by ICI Americas, Inc.). The concentration of a particular surfactant or total surfactant present in the aqueous phase may be selected to stabilize emulsion droplets prior to heating. An exemplary concentration of surfactant for the aqueous phase is about 0.01 to 10%, 0.05 to 5%, 0.1 to 1%, or 0.5% by weight, among others. In some cases, a skin-forming protein may function as a surfactant, although proteins generally are not classified as surfactants for the purposes of the present disclosure.

Skin-Forming Components

The aqueous phase may include one or more skin-forming components. A skin-forming component is any substance that promotes formation of a skin near or at the droplet boundary, for example, by serving as a structural element of the skin. Each skin-forming component may have any suitable distribution with respect to each droplet prior to skin formation. The skin-forming component may be localized selectively near or at the droplet interface, to form an interface layer, or may be distributed more uniformly throughout the aqueous phase. If distributed more uniformly, the skin-forming component may be recruited to the interface during skin formation.

The skin-forming components may include at least one skin-forming protein. The protein may be present at an effective concentration, which is an amount sufficient for detectable skin formation under the appropriate conditions (e.g., heating). Exemplary effective concentrations include at least about 0.01% or 0.03%, 0.03% to 3%, 0.05% to 2%, 0.1% to 1%, or about 0.1% by weight, among others. The protein may be described as a "non-specific blocking" or "non-specific binding" protein. The phrase "non-specific blocking" or "non-specific binding" as used herein refers generally to a capability to non-specifically bind to surfaces, that is, hydrophobic and/or hydrophilic surfaces, sometimes with the aid of heating. Non-specific blocking/binding proteins are typically water-soluble proteins, may be relatively large serum or milk proteins (among others), and/or may not interact with any of the other components of the aqueous phase in a specific binding fashion. Exemplary non-specific blocking/binding proteins that may be suitable as skin-forming proteins include albumins (such as a serum albumin (e.g., from bovine (BSA), human, rabbit, goat, sheep or horse, among others)), globulins (e.g., beta-lactoglobulin), casein, and gelatin (e.g., bovine skin gelatin type B), among others.

Additional Additives

The aqueous phase optionally further includes any of a variety of additives. The additives, may, for example, be intended to act as preservatives, enzyme enhancers, enzyme inhibitors, cofactors, and the like, including, for example, sodium azide, betaine, trehalose, and RNase inhibitors, among others. Other exemplary additives are enzymes, such as a restriction enzyme, a ligase, a reverse transcriptase, Uracil-DNA N-Glycosylase (UNG), and the like.

Treatment Prior to Droplet Formation

The sample and/or the aqueous phase may be treated, prior to droplet generation, to facilitate formation of droplets. Treatment may be particularly suitable with a relatively high concentration and/or relatively long fragments of nucleic acid in the aqueous phase. When droplets are formed under standard conditions, the aqueous phase may be subjected to a rapid decrease in cross sectional area, elongation, followed by separation and formation of the droplet. When DNA, RNA, or another long-chain polymer is present above certain concentrations, the ability to form droplets may be impaired. For example, these polymers may become entangled with each other in the rapid process of droplet formation, and may not have sufficient time to separate through diffusion, there forming a cord that causes the droplets not to form efficiently. The cord may result in jetting, microsatellites, and coalescence, and other features of poor emulsion formation. Alternatively, or in addition, the polymers may be interacting with the droplet interface, decreasing surface tension and preventing droplet formation.

In any event, an approach is needed to overcome this effect on droplet formation. One exemplary approach is to slow down the rate of droplet formation so that the droplet has time to pinch off and form. However, this approach reduces the throughput of droplet formation. Another mechanical solution may be to redesign the droplet generator to force the formation of droplets under these high concentration conditions. Another exemplary approach is to fragment the polymer(s) to a smaller size. The polymer may be fragmented by heating the aqueous phase before emulsion formation. For example, the aqueous sample may be heated to at least about 80° C., 90° C., or 95° C. for at least about 1, 2, 5, 10, 15, or 30 minutes, among others. Suitable heating may result in the ability to form droplets at high DNA concentrations under normal conditions. A further exemplary approach is to fragment DNA in the aqueous phase by digesting the DNA with a restriction enzyme, which targets specific sites (or cuts the DNA nonspecifically). As long as the specific sites are outside of the target of interest, the copy number of target measured is preserved in the sample. The digestion may or may not go to completion. In many cases, only a partial digestion may be necessary to reduce the average DNA fragment size to a level that does not impact droplet formation.

Selected Embodiments of the Aqueous Phase

The aqueous phase may be formulated to perform one or more enzyme reactions, such as reverse transcription, amplification, restriction enzyme digestion, ligation, uracil cleavage from carry-over amplicons (to prevent amplification of contaminating targets), any combination thereof, or the like. For example, the aqueous phase may be formulated to perform RT-PCR and may include any suitable combination of the components listed in the follow formulations:

Aqueous Phase Formulation 1
  Reaction Buffer (~50-70 mM [salt]): ~45-55 mM KCl, ~10-15 mM Tris, ~pH 7.5-8.5)
  $MgCl_2$ and/or $MgSO_4$ (~1.5-5 mM)
  BSA or bovine gelatin (~0.1-1% w/v)
  Nonionic polyethylene oxide (PEO)/polypropylene oxide (PPO) block copolymer surfactant (~0.1-1% w/v)
  Heat-stable Polymerase (~0.04 Units/µL)
  Reverse Transcriptase (~0.04 Units/µL)
  dNTPs (~200-400 µM each (dATP, dCTP, dGTP, dTTP) or ~300-500 µM each (with dUTP in place of dTTP))
  UNG (Uracil-DNA N-Glycoslyase) (optional; ~0.025-0.1 Units/µL)
  Total nucleic acid (~pg to ng range/nL, with the target nucleic acid present at less than ~10 copies/nL or less than ~1 copy/nL)
  Primers (~0.1-1.0 µM)
  Probe(s) for Fluorescence Detection (~0.1-0.25 µM)

Aqueous Phase Formulation 2 (Selected Components)
  KCl (~50 mM)
  Tris (~15 mM, pH 8.0)
  $MgCl_2$ (~3.2 mM)
  BSA or bovine gelatin (~0.1% w/v)
  Pluronic F-68 (surfactant, ~0.5% w/v)
  dNTPs (~200 µM each (dATP, dCTP, dGTP, dTTP))
  Primers (~0.5 µM each)
  Probe(s) for Fluorescence Detection (~0.25 µM)

IV. NONAQUEOUS PHASE

The nonaqueous phase may serve as a carrier fluid forming a continuous phase that is immiscible with water, or the nonaqueous phase may be a dispersed phase. The nonaqueous phase may be referred to as an oil phase comprising at least one oil, but may include any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others.

In exemplary embodiments, the oil is a fluorinated oil, such as a fluorocarbon oil, which may be a perfluorinated organic solvent. A fluorinated oil may be a base (primary) oil or an additive to a base oil, among others. Exemplary fluorinated oils that may be suitable are sold under the trade name FLUORINERT (3M), including, in particular, FLUORINERT Electronic Liquid FC-3283, FC-40, FC-43, and FC-70. Another example of an appropriate fluorinated oil is sold under the trade name NOVEC (3M), including NOVEC HFE 7500 Engineered Fluid.

Surfactants

As discussed above with respect to the aqueous phase, a surfactant is a surface-active substance capable of reducing the surface tension of a liquid in which it is dissolved, and may incorporate both a hydrophilic portion and a hydrophobic portion, which may collectively confer a dual hydrophilic-hydrophobic character on the surfactant. In contrast to the surfactant present in the aqueous phase, the nonaqueous phase would typically incorporate a hydrophobic surfactant. The nonaqueous phase may include one or more surfactants, each of which may be disposed/dissolved in the nonaqueous phase prior to, during, and/or after capsule formation. The surfactants may include a nonionic surfactant, an ionic surfactant (a cationic (positively-charged) or anionic (negatively-charged) surfactant), or both types of surfactant. Exemplary anionic surfactants that may be suitable include carboxylates, sulphonates, phosphonates, and so on. The one or more surfactants may be present, individually or collectively, at any suitable concentration, such as greater than about 0.001% or 0.01%, or about 0.001% to 10%, 0.05% to 2%, or 0.05% to 0.5%, among others.

An ionic surfactant (e.g., a negatively-charged surfactant) may be preferred for capsule formation. The ionic surfactant may promote attraction for the purpose of assembly of components at the interface that can lead to the formation of a skin upon heating. For example, ionic pairing may occur between an ionic surfactant in the continuous phase and a skin-forming protein in the dispersed phase (or vice versa if the continuous phase is aqueous). With the skin-forming protein bound at the interface by the ionic surfactant, application of heat may change the conformation of the protein (by denaturation) and/or decrease its solubility in the aqueous phase, which may lead to formation of skin. Alternatively, or in addition, if an ionic or nonionic surfactant is included in an oil composition used for emulsion formation, hydrophobic interactions may recruit a skin-forming protein and/or other skin-forming material to the interface.

The one or more surfactants present in the nonaqueous phase (or oil phase) may be fluorinated surfactants (e.g., surfactant compounds that are polyfluorinated and/or perfluorinated). Exemplary fluorinated surfactants are fluorinated polyethers, such as carboxylic acid-terminated perfluoropolyethers, carboxylate salts of perfluoropolyethers, and/or amide or ester derivatives of carboxylic acid-terminated perfluoropolyethers. Exemplary but not exclusive perfluoropolyethers are commercially available under the trade name KRYTOX (DuPont), such as KRYTOX-FSH, the ammonium salt of KRYTOX-FSH ("KRYTOX-AS"), or a morpholino derivative of KRYTOX-FSH ("KRYTOX-M"), among others. Other fluorinated polyethers that may be suitable include at least one polyethylene glycol (PEG) moiety.

A primary surfactant, such as a fluorinated polyether, may be present at any suitable concentration, such as about 0.02% to 10%, or about 1% to 4%, by weight. The primary surfactant may be present at either a relatively higher concentration (about 1% or greater by weight) or a relatively lower concentration (less than about 1% by weight, such as about 0.02 to 0.5% by weight). In some cases, use of the lower concentration may enable capsules to be created by heating droplets without use of an overlay and without substantial droplet breakage. The primary surfactant may (or may not) have a molecular weight of at least about 1, 2, or 5 kilodaltons.

The nonaqueous phase may further include one or more additional surfactants selected to modify one or more physical properties of a selected oil. For example, an additional surfactant may be used to lower the evaporation potential of the selected oil. By lowering the evaporation potential, the additional surfactant may reduce or minimize the effect of evaporation on droplets at an emulsion-air interface. In exemplary embodiments, the nonaqueous phase may include a fluorinated oil, which may be the predominant component, a primary surfactant (e.g., a fluorinated polyether), and a secondary/additional surfactant, among others. The secondary/additional surfactant may be a fluorinated alcohol with only one (a monoalcohol) or two hydroxyl groups, such as perfluorodecanol or perfluorooctanol, among others. The additional surfactant may have a molecular weight of less than about 1000 or 500 daltons, may have no more than about 20, 15, or 12 carbons, and may be present at a concentration of about 0 to 10%, 0% to 5%, 0 to 2.5%, 0.1% to 2.5%, or 0.001% to 0.5% by weight, among others.

Selected Embodiments of the Nonaqueous Phase

The nonaqueous phase may include any combination of a fluorosurfactant, a fluorinated oil, one or more fluorinated additives to lower evaporation potential, and one or more fluorinated co-surfactants, among others. The following formulations correspond to exemplary embodiments of the nonaqueous phase of the present disclosure.

Oil Phase Formulation 1 (High surfactant)
 HFE 7500 fluorinated oil
 KRTOX-AS and/or KRYTOX-M (~1-4% w/w)
Oil Phase Formulation 2
 HFE 7500 fluorinated oil
 KRYTOX-AS and/or KRYTOX-M (~0.45-2.85% w/w)
 Perfluorodecanol (~0.009-2.25% w/w or ~1.8% w/w)
Oil Phase Formulation 3
 HFE 7500 fluorinated oil
 KRYTOX-AS or KRYTOX-M (~1.8% w/w)
 Perfluorodecanol (~0.18% w/w)
Oil Phase Formulation 4
 FC-40 fluorinated oil
 KRYTOX-AS and/or KRYTOX-M (~0.45-2.85% w/w or ~1.8% w/w)
 Perfluorodecanol (~0.009-2.25% w/w or ~0.18% w/w)
Oil Phase Formulation 5
 FC-43 fluorinated oil
 KRYTOX-AS and/or KRYTOX-M (~0.45-2.85% w/w or ~1.8% w/w)
 Perfluorodecanol (~0.009-2.25% w/w or ~0.18% w/w)

Oil Phase Formulation 6
  FC-70 fluorinated oil
  KRYTOX-AS and/or KRYTOX-M (~0.45-2.85% w/w or ~1.8% w/w)
  Perfluorodecanol (~0-2.25% w/w or ~0.18% w/w)
Oil Phase Formulation 7 (Low surfactant)
  HFE 7500 fluorinated oil solvent
  KRTOX-AS and/or KRYTOX-M (greater than ~0.01 to 0.5% w/w, ~0.02 to 0.5% w/w, or ~0.18% w/w)

V. FORMATION OF EMULSIONS

The aqueous and nonaqueous phases containing the components discussed above may be provided (e.g., obtained and/or prepared), and then utilized to form an emulsion.

An emulsion generally includes droplets of a dispersed phase (e.g., an aqueous phase) disposed in an immiscible continuous phase (e.g., a nonaqueous phase such as an oil phase) that serves as a carrier fluid for the droplets. Both the dispersed and continuous phases generally are at least predominantly liquid. The emulsion may be a water-in-oil (W/O) emulsion, an oil-in-water (O/W) emulsion or a multiple emulsion (e.g., a W/O/W or a W/O/W/O emulsion, among others).

Any suitable method and structure may be used to form the emulsion. Generally, energy input is needed to form the emulsion, such as shaking, stirring, sonicating, agitating, or otherwise homogenizing the emulsion. However, these approaches generally produce polydisperse emulsions, in which droplets exhibit a range of sizes, by substantially uncontrolled generation of droplets. Alternatively, monodisperse emulsions (with a highly uniform size of droplets) may be created by controlled, serial droplet generation with at least one droplet generator. In exemplary embodiments, the droplet generator operates by microchannel flow focusing to generate an emulsion of monodisperse droplets. Other approaches to and structures for droplet generation that may be suitable are described above in the documents listed above under Cross-References, which are incorporated herein by reference, particularly U.S. Provisional Patent Application Ser. No. 61/341,218, filed Mar. 25, 2010; U.S. Provisional Patent Application Ser. No. 61/409,106, filed Nov. 1, 2010; U.S. Provisional Patent Application Ser. No. 61/409,473, filed Nov. 2, 2010; U.S. Provisional Patent Application Ser. No. 61/410,769, filed Nov. 5, 2010; U.S. patent application Ser. No. 12/862,542, filed Aug. 24, 2010; and U.S. Patent Application Publication No. 2010/0173394 A1, published Jul. 8, 2010.

A surfactant present in the aqueous phase may aid in the formation of aqueous droplets within a nonaqueous phase. The surfactant may do so by physically interacting with both the nonaqueous phase and the aqueous phase, stabilizing the interface between the phases, and forming a self-assembled interfacial layer. The surfactant generally increases the kinetic stability of the droplets significantly, substantially reducing coalescence of the droplets, as well as reducing aggregation. The droplets (before transformation to capsules) may be relatively stable to shear forces created by fluid flow during fluidic manipulation. For example, the droplets may be stable to flow rates of at least 40 µL/min or 50 µL/min in a 100 µm or 200 µm channel using selected combinations of nonaqueous and aqueous phase formulations.

The resulting droplets may have any suitable shape and size. The droplets may be spherical, when shape is not constrained. The average diameter of the droplets may be about 1 to 500 µm, 5 to 500 µm, or 50 to 500 µm, and the average volume of the droplets may be about 50 pL to 500 nL, or 100 pL to 10 nL, among others.

The droplets may be formed and then collected as an emulsion in a reservoir, such as vial, a test tube, a well of a plate, a chamber, or the like. In some embodiments, the droplets may be collected as an emulsion in a PCR vial or plate, which is then thermocycled. Alternatively, or in addition, the droplets may be collected in a reservoir and then transferred to a different container for thermocycling and/or may be manipulated and/or transported via fluidics, such as microfluidics.

VI. DROPLET TRANSFORMATION

Droplets may be transformed into capsules in which the droplets are encapsulated by a skin. Generally, droplets are transformed by heating. The droplets, the continuous phase, and/or the emulsion may be heated to a temperature sufficient for skin formation and for a time sufficient to produce the skin. An inverse relationship may exist between the temperature and the time sufficient for such a conversion to occur. That is, heating the droplets at a relatively low temperature may require a longer heating time than heating the droplets at a relatively higher temperature. However, skin formation may occur rapidly above a threshold temperature and much more slowly a few degrees below the threshold temperature. For example, skin formation may occur or be complete in less than about five minutes or less than about one minute when the emulsion is heated above the threshold temperature. In any event, transformation of droplets into capsules may decrease the solubility of one or more skin-forming proteins (and/or other skin-forming material(s)) in the aqueous phase (i.e., the dispersed phase or continuous phase), such that the proteins/materials become less soluble (e.g., substantially insoluble) in the aqueous phase. Accordingly, the skin may be substantially insoluble in the aqueous phase.

In some embodiments, the threshold temperature may correspond to the denaturation temperature of a skin-forming protein in the aqueous phase. Accordingly, formation of the skin may be a consequence of protein denaturation that occurs much more rapidly above the threshold temperature than below. As an example, BSA has been reported to denature at about 50° C. to 55° C., and droplets incorporating BSA as a skin-forming protein are induced to form a skin rapidly at about the same temperature. Accordingly, use of another skin-forming protein with a different denaturation temperature may require heating to a corresponding different temperature before skin is formed.

Heating the droplets to a temperature above 55° C. may convert a self-assembled interfacial layer to an interfacial skin. The skin may be composed of protein, or protein and surfactant, among others. In some cases, the droplets may be heated via thermal cycling, such as is performed during PCR amplification. The thermal cycling profile may include variations in temperature from about 4° C. to about 99° C. The droplets optionally may be heated via thermal cycling as a result of transport of the droplets through a flow-based thermocycling system. Further aspects of an exemplary flow-based thermocycling system are disclosed in U.S. Patent Application Publication No. 2010/0173394 A1, published Jul. 8, 2010, which is incorporated herein by reference.

VII. CAPSULES

Capsules enclose droplets in a skin, which can be visualized microscopically when wrinkled, deformed, or damaged. The skin is a solid or semi-solid phase disposed interfacially, that is, near or at an interface between each droplet boundary and the continuous phase. Accordingly, in contrast to the fluid interface present in standard droplets, a decrease in capsule volume generally results in a microscopically visible change in appearance of the skin. The skin may lose its smooth spherical geometry, as less tension is applied to the skin, and appear somewhat wrinkled or shriveled, reflecting a substantial degree of solidity. For example, the presence (or absence) of a skin may be detected by spreading capsules/droplets on a microscope slide, encouraging capsule/droplet shrinkage through evaporation, and then observing the capsules/droplets under a microscope. Similarly, when the capsules are exposed to a non-optimal spacing fluid and/or are subjected to excessive shear force, the skin may tear, leaving distinct openings, with ragged edges, in the skin itself (e.g., see Example 3).

The skin may remain pliant and flexible, such that the capsules are viscoelastic. However, by suffering deformation and physical damage that is readily observed visually (e.g., via microscope), the skins are revealed to be at least substantially semi-solid or solid, and not a freely deformable liquid.

The enhanced stability of the capsule, relative to the original droplet formulation, is reflected in the stability of the capsule with respect to physical manipulation. The capsules may be transported, sorted, flow focused, and dispensed with little or no damage to the capsule wall (i.e., the skin). In contrast to the precursor droplets, the capsules may be stable to fluidic processing operations that generate relatively high shear. For example, the capsules may be stable in fluid flowing at a flow rate of up to at least about 200, 300 or 400 µL/min in a channel with a diameter of about 125 µm or less or about 250 µm or less, among others, and/or may be stable flowing through 90-degree turns (as may be formed by valves).

The capsules may be used in any suitable manner. The capsules may be collected, manipulated, and/or sorted. They may be used in an assay or other biomedical application, or may be collected and stored. The capsules disclosed herein are typically stable with respect to storage, and may be stored at room temperature for one month or longer. The capsules may be stored at a wide range of temperatures, but preferably from about 4° C. to about 40° C., among others.

A portion (e.g., a majority) of the continuous phase may be removed prior to heating of the droplets to create capsules. Where the majority of the continuous phase has been removed, the resulting capsules may occupy a high fraction of the emulsion, resulting in a composition that resembles a gel in some respects. The capsules may be densely packed in such cases and, where the capsules originate from monodisperse droplets, may pack in a highly ordered arrangement.

Where the continuous phase is not removed prior to heating, the resulting composition typically resembles a fluid. Although the capsules may settle into a close-packed arrangement, agitation of the composition typically results in dispersion of the capsules in the continuous phase.

VIII. SPACING FLUID

A spacing fluid may be added to the emulsion. The spacing fluid generally is miscible with the current/original continuous phase of the emulsion and may have the same composition as, or a different composition from, the current/original continuous phase. Accordingly, the spacing fluid may be nonaqueous or aqueous, based on the type of emulsion to which the fluid is being added.

For use with a water-in-oil emulsion, the spacing fluid may include the same base oil as the continuous phase or a different base oil. (A base oil is the predominant or primary oil (or oils) in an oil (continuous) phase.) For example, the continuous phase may have a fluorinated oil as the base oil, and the spacing fluid may have the same (or a different) fluorinated oil as its base oil.

In exemplary embodiments, the spacing fluid includes a different surfactant than the continuous phase, and/or substantially less total surfactant by weight than the continuous phase (e.g., at least about 2-, 5-, 10-, or 100-fold less total surfactant, among others). Alternatively, or in addition, the spacing fluid may have no surfactant that is present at a concentration above the critical micelle concentration of the surfactant (which includes having at least substantially no surfactant at all). Use of a concentration of surfactant below its critical micelle concentration may minimize unwanted formation of new droplets, while providing a cleaning function in a flow system. Also, with some emulsion formulations, use of the same surfactant and approximately the same amount of surfactant in the spacing fluid as in the original continuous phase of the emulsion may cause capsules to shrink, shrivel, and/or rupture, which permits the skin to be visualized microscopically. Exemplary effects of distinct spacing fluids on capsule integrity are described below in Example 3.

In some examples, the continuous phase and the spacing fluid both may contain ionic (primary) fluorosurfactants, or the continuous phase may contain an ionic (primary) fluorosurfactant and the spacing fluid a nonionic (primary) fluorosurfactant. If both contain an ionic fluorosurfactant, the primary fluorosurfactant concentration may be selected to be substantially lower in the spacing fluid than in the continuous phase. Otherwise, if the concentration of the ionic fluorosurfactant in the spacing fluid is too high, the ionic fluorosurfactant may draw water out of the capsules, causing them to shrink (which may wrinkle/tear the skin). If a non-ionic fluorosurfactant is used in the spacing fluid, then capsule shrinkage generally does not occur at either low or high concentrations of surfactant. However, shrinkage may depend on the purity of the non-ionic surfactant. If a non-ionic surfactant is not 100% pure, ionic impurities may exist (such as reactive precursors or reaction by-products). At higher concentrations of an impure non-ionic surfactant, these ionic impurities may reach a concentration high enough to cause damage to the capsules (e.g., by withdrawal of water from the capsules to cause shrinkage or breakage). In any event, the nonionic fluorosurfactant may be present in the spacing fluid at a substantially lower, about the same, or a substantially higher concentration than the primary (or total) surfactant in the continuous phase (and/or an oil phase or oil composition used to form an emulsion).

The spacing fluid may be formulated according to the nonaqueous phases presented above in Section IV. Additional exemplary formulations for a spacing fluid are as follows:

Spacing Fluid Formulation 1
    HFE 7500, FC-40, FC-43, and/or FC-70 fluorinated oil
    Perfluorinated alcohol (~0-10% w/w or ~0.18% w/w)
    KRTOX-AS and/or KRYTOX-M (0-0.1%, 0-0.01%, or 0-0.001% w/w)

Spacing Fluid Formulation 2
    HFE 7500, FC-40, FC-43, and/or FC-70 fluorinated oil
    Pegylated-fluorosurfactant (0-0.1%, 0-0.01%, 0-0.001%, or 0.00001% w/w)

IX. CAPSULE AND DATA PROCESSING

The capsules of the present disclosure, once prepared, may be processing. Processing may include subjecting the capsules to any condition or set of conditions under which at least one reaction of interest can occur (and/or is stopped), and for any suitable time period. Accordingly, processing may include maintaining the temperature of the capsules at or near a predefined set point, varying the temperature of the capsules between two or more predefined set points (such as thermally cycling the capsules), exposing the capsules to light, changing a pressure exerted on the capsules, applying an electric field to the capsules, or any combination thereof, among others.

Signals may be detected from the capsules before, during, and/or after processing. The signals may be detected optically, electrically, chemically, or a combination thereof, among others. The signals may correspond to at least one reaction of interest performed in the capsules. In exemplary embodiments, the signals may be detected as fluorescence signals, which may include two or more types of signals distinguishable fluorescence signals.

Data corresponding to the detected signals may be processed. Data processing may determining an assay result for each encapsulated assay mixture analyzed, which may be an analog or digital value.

X. EXAMPLES

The following examples describe selected aspects and embodiments of the present disclosure related to systems for making and using emulsions, particularly emulsions including droplets encapsulated by a skin. These examples are intended for illustration and should not limit the entire scope of the present disclosure.

Example 1. Selective Removal of Continuous Phase from an Emulsion

This example describes an exemplary approach 80 to removing a continuous phase 82 selectively (relative to a dispersed phase 83) from an emulsion 84, to increase the volume fraction occupied by droplets (or capsules) 86; see FIG. 3.

Emulsion 84 may be held by a reservoir 88 having a port 90. The port may be formed near or at the bottom of the reservoir, if droplets 86 are buoyant in the continuous phase (as shown here), or may be formed at a higher position of the reservoir if the droplets sink in the continuous phase.

Buoyant droplets may move within the continuous phase over time toward the top of the emulsion, in a process termed creaming, if the droplets initially have a more uniform distribution in the entire volume of the continuous phase. As a result, the droplets accumulate over time in an upper region of the continuous phase, to form a droplet layer 92 of aggregated droplets that grows downward as buoyant droplets are added to the bottom of the layer. A lower portion 94 of the emulsion becomes progressively depleted of droplets as droplets migrate upward to layer 92. The density difference between the aqueous phase and the continuous phase, and the viscosity of the continuous phase, determine how much time (e.g., seconds, minutes, or hours) is needed for most of the droplets to join layer 92. In any event, a pressure drop may be created between the top of the emulsion and port 90, to drive lower portion 94 of continuous phase 82 selectively from the reservoir, indicated at 96, via port 90. For example, pressure, indicated at 98, may be applied to the top of the emulsion, such as by regulating air pressure above the emulsion, or a vacuum may be applied to port 90 to draw the continuous phase through the port. In any event, a concentrated emulsion 99 produced after selective removal of continuous phase 82 is shown in the right half of FIG. 3. In other embodiments, droplets that sink in the continuous phase may be driven through port 90 to separate droplets from an upper portion of the continuous phase.

Example 2. Overlaying an Emulsion

Figure 4:
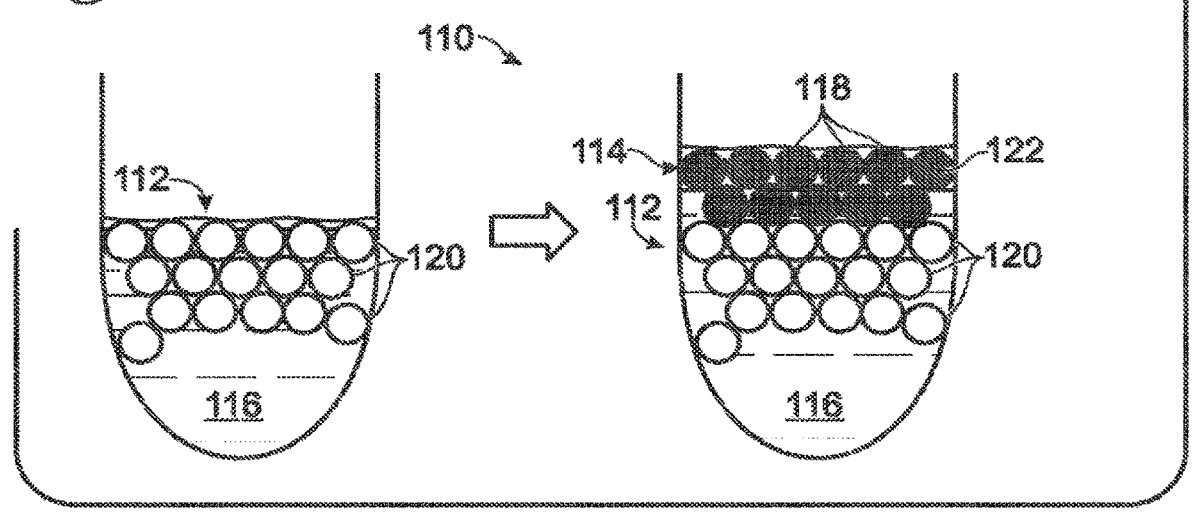
FIG. 4 is a schematic illustration of an exemplary approach of covering a primary emulsion with an overlay emulsion, in accordance with aspects of the present disclosure.
Figure 5:
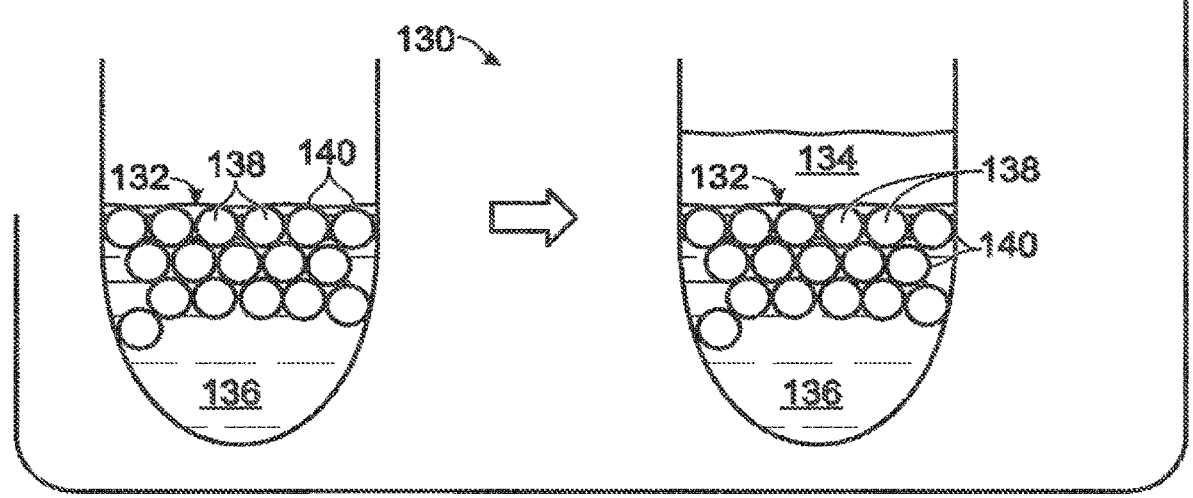
FIG. 5 is a schematic illustration of an exemplary approach of covering an emulsion with an overlay phase that is immiscible with at least the continuous phase of the emulsion, in accordance with aspects of the present disclosure.

This example describes exemplary approaches to overlaying an emulsion with liquid; see FIGS. 4 and 5. The use of an overlay may be suited for use with an emulsion having buoyant droplets. In this case, buoyancy causes droplets to collect near the interface of the emulsion with air, which renders the droplets less protected by the continuous phase and more vulnerable to evaporative loss. Also, the presence of an air interface may render the emulsion more susceptible to heat-induced damage to droplets (e.g., droplet breakage).

FIG. 4 illustrates an approach 110 to overlaying an emulsion 112 by using an overlay emulsion 114. The overlay emulsion may or may not have substantially the same continuous phase 116 as underlying or primary emulsion 112, but generally has a continuous phase that is miscible with the continuous phase of the primary emulsion. The overlay emulsion may include aqueous overlay droplets 118 that are distinguishable from droplets 120 in the underlying emulsion, such as based on size, a difference in detectability, or the like. For example, the overlay droplets may be "blanks" or "dummy" droplets that lack the probe(s), label(s), and/or marker(s) that is present in the underlying (sample) droplets. These "blank" droplets can be configured to produce no interfering signal during detection of assay signals. Alternatively, or in addition, the overlay droplets may include a visible dye 122 that permits the presence, position, and integrity of the overlay to be seen by eye without interfering with assay results. The visible dye may be a compound that is at least substantially nonfluorescent, such as bromphenol blue or Allura Red, among others. In any event, the overlay droplets, even if the same density as the underlying sample droplets, will tend to remain above the sample droplets to form a distinct droplet layer, as shown schematically in the figure. The overlay droplets may serve as sacrificial droplets that are selectively damaged when the primary emulsion and overlay emulsion are heated (such as during thermal cycling), because the overlay droplets are closer to the air interface.

Overlay droplets may be placed over sample droplets before any of the droplets (overlay or sample) are transformed by heat to capsules. Alternatively, overlay droplets can be pre-treated with a heat incubation step to transform the droplets into overlay capsules before the overlay capsules are placed over sample droplets.

Furthermore, overlay droplets/capsules may be used as a control/calibrator for an assay system. For example, these droplets/capsules can be blank or configured to have an indicator (such as a dye) to be used as a control/standard that provides information about an instrument or process that sample droplets/capsules are exposed to, including thermal cycling, detection of assay analytes in flow, and so on. In exemplary embodiments, dye-loaded overlay droplets/capsules can be used as controls/standards for calibrating a detector or detection method, such as providing signals that correspond to amplification-positive and/or amplification-negative droplets/capsules. Further aspects of using droplets as controls/calibrators are described in U.S. Patent Application Publication No. 2010/0173394 A1, published Jul. 8, 2010, which is incorporated herein by reference.

Blank capsules (or droplets) also can be used in a carrier fluid to clean, and/or assess the cleanliness of, an instrument within which sample capsules (or droplets) are transported. The blank capsules can, for example, be introduced after a detection run of sample capsules, to follow the sample capsules along a flow path through a detection region of the instrument. The blank capsules may help to urge residual sample capsules along the flow path, such as by mechanically shearing away such residual capsules. Accordingly, the use of blank capsules may help to determine if unwanted sample capsules are still remaining in the instrument (which could contaminate future runs of sample capsules).

Non-sample capsules (or droplets) therefore may be useful as part of an overlay (to protect sample droplets/capsules from breakage and/or degradation) or when used separately from sample droplets/capsules. In other words, non-sample capsules can serve multiple functions in some cases.

FIG. 5 shows an approach 130 to covering an emulsion 132 with an overlay phase 134. The overlay phase is immiscible with underlying continuous phase 136 of the emulsion, and optionally immiscible with an aqueous phase 138 that composes droplets 140 of emulsion 132. The overlay phase also may have a lower density than continuous phase 136 and, optionally, aqueous phase 138. For example, the underlying continuous phase may be formed at least predominantly of fluorinated oil and the overlay phase may be formed at least predominantly of fluorophobic and/or lipophilic oil, such as a hydrocarbon oil (e.g., mineral oil). In some embodiments, overlay phase 134 may be aqueous, and phases 134 and 138 may have at least substantially the same density and/or composition of salt, buffer, and/or surfactant, among others. In other words, the overlay phase may have a similar composition to the aqueous phase and/or may be osmotically balanced with respect to the aqueous phase. Accordingly, an aqueous overlay phase may include any combination of the components described above in Section III, such as salt, buffer, protein, surfactant, a visible dye as described above, or any combination thereof, among others.

Example 3. Spacing Fluids and Capsule Damage

This example describes exemplary spacing fluids with distinct effects on capsule shape and integrity, and presents micrographs showing these effects; see FIGS. 6A, 6B, and 7A-D.

Figure 6A:
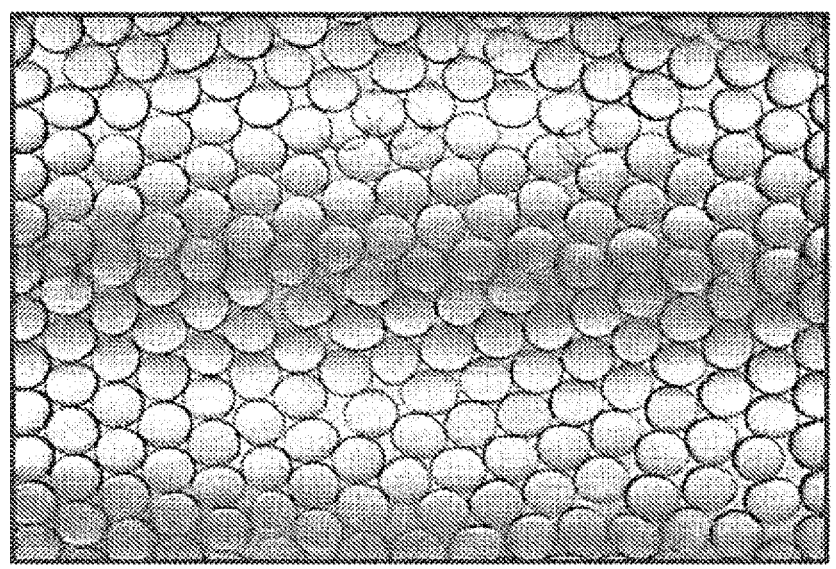
FIG. 6A and FIG. 6B are a pair of micrographs of capsules that have been exposed to a spacing fluid composed of an oil phase lacking the surfactant that was present during droplet generation (FIG. 6A) or containing the surfactant (FIG. 6B), in accordance with aspects of the present disclosure.
Figure 6B:
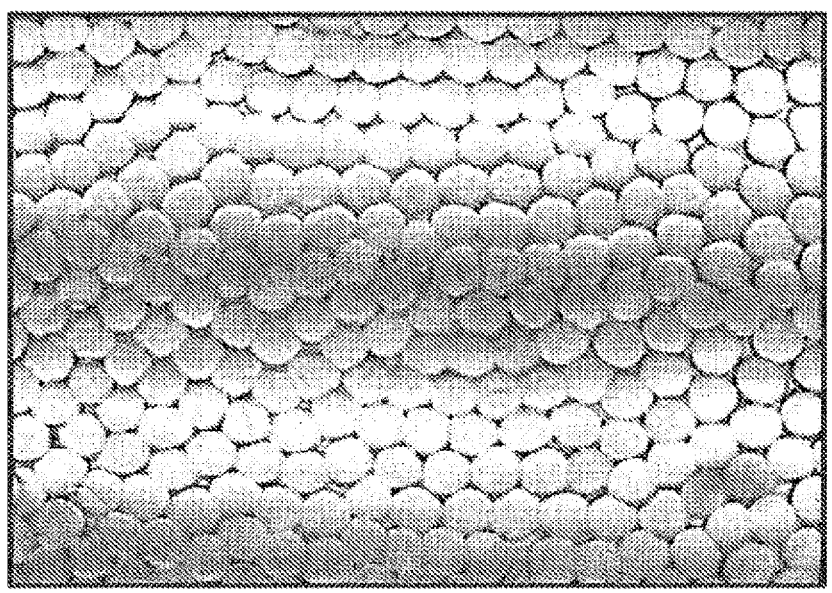
Figure 7B:
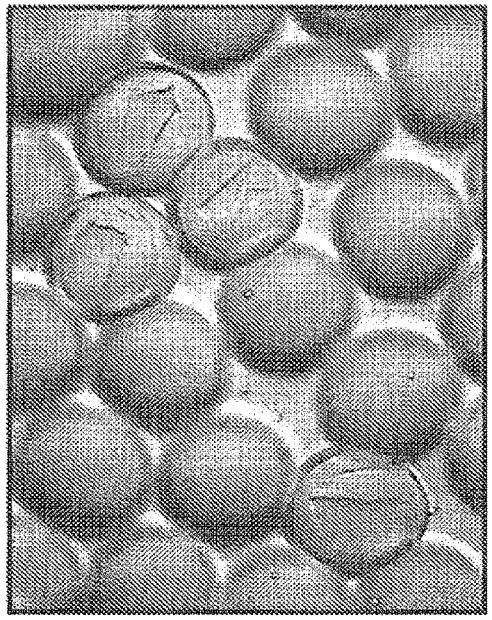
FIG. 7A-FIG. 7D are a set of micrographs of capsules formed as in FIGS. 6A and 6B and exposed to the same spacing fluid as in FIG. 6B but viewed at higher magnification, in accordance with aspects of the present disclosure.
Figure 7D:
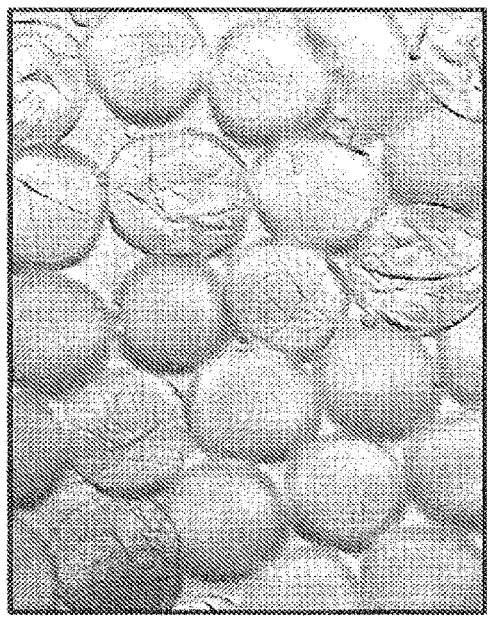
Figure 7A:
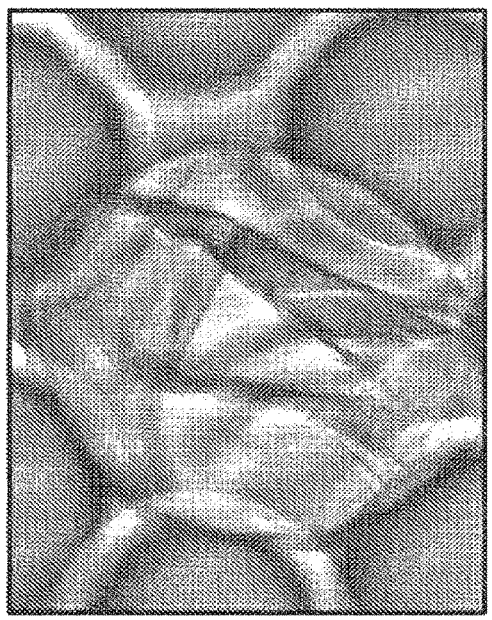
Figure 7C:
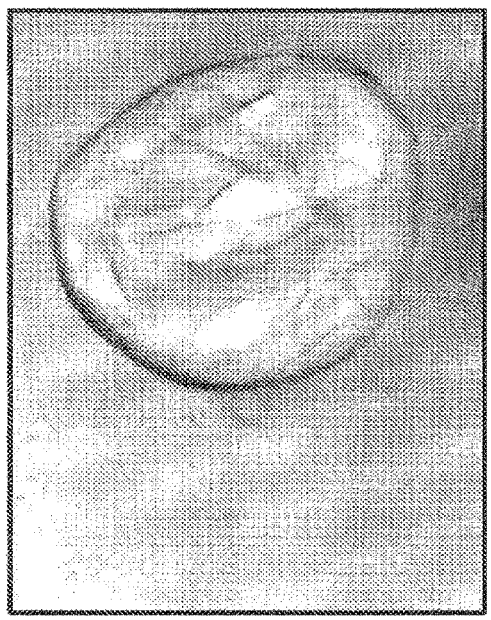

FIGS. 6A and 6B show a pair of micrographs of capsules from emulsions that have been exposed to a spacing fluid composed of a base oil without surfactant (FIG. 6A) or with surfactant (FIG. 6B). Droplets were generated in HFE 7500 fluorinated oil with 1.8% w/w of Krytox-AS as surfactant. Excess continuous phase was removed, and then the droplets were heated to form capsules. A spacing fluid was added to the continuous phase, which substantially increased the volume fraction of the continuous phase in the emulsion. The spacing fluid was either base oil (HFE 7500) without surfactant (FIG. 6A) or with surfactant at the same concentration as for droplet generation (1.8% w/w of Krytox-AS). In other words, the spacing fluid had the same composition as the original continuous phase (FIG. 6B) or was the same except that the surfactant was omitted (FIG. 6A).

The absence or presence of surfactant in the spacing fluid can have a dramatically different effect on capsule shape and integrity. FIG. 6A shows that, without surfactant in the spacing fluid, capsule boundaries in FIG. 6A appear smooth and spherical. In other words, elimination of surfactant from the spacing fluid may have no negative effect on capsule shape and integrity when the spacing fluid is added to the continuous phase. FIG. 6B shows that, with the same surfactant in the spacing fluid and continuous phase, and at the same concentration, the capsules appear to shrink and shrivel. The capsule boundaries become more irregular and wrinkled and less spherical.

FIG. 7 shows a set of micrographs of capsules treated as in FIG. 6B but viewed at higher magnification. Many of the capsules exhibit a skin that has been damaged. The skin is often wrinkled and in many cases torn, with ragged edges visible.

Example 4. Selected Embodiments I

This example describes selected aspects and embodiments related to preparation and use of emulsions containing capsules, presented without limitation as a series of numbered paragraphs.

1. A method of preparing stable capsules of an aqueous phase, comprising: (A) preparing an aqueous phase including a buffering agent, a first surfactant at a concentration of 0.1 to 1.0% by weight, and a non-specific binding protein at a concentration of 0.1 to 1.0% by weight; (B) preparing an organic phase including a fluorinated oil and a fluorinated surfactant; (C) forming droplets of the aqueous phase disposed within the organic phase, where each droplet has a defined droplet boundary; and (D) heating the droplets sufficiently to convert the droplet boundary to a semi-solid or solid skin that encapsulates the aqueous phase.

2. The method of paragraph 1, wherein the first surfactant is a nonionic surfactant.

3. The method of paragraph 1, wherein the fluorinated surfactant is a nonionic surfactant or an anionic surfactant.

4. The method of paragraph 1, wherein the fluorinated surfactant is a carboxylic acid-terminated perfluoropolyether, an ammonium salt of a carboxylic acid-terminated perfluoropolyether, or a morpholino derivative of a carboxylic acid-terminated perfluoropolyether.

5. The method of paragraph 1, wherein the formed droplets are non-coalescing, stable to flocculation, and stable with respect to flow rates of at least 40 µL/min.

6. A method of sample analysis within discrete encapsulated droplets, comprising: (A) preparing an aqueous phase including a PCR reaction buffer, a magnesium salt, a nonionic surfactant that is a block copolymer of polypropylene oxide and polyethylene oxide at a concentration of 0.1 to 1.0% by weight, a blocking protein at a concentration of 0.1 to 1.0% by weight, a heat-stable polymerase, dNTPs, and a target nucleic acid; (B) preparing an organic phase including a fluorinated oil and a fluorinated surfactant; (C) forming droplets of the aqueous phase disposed within the organic phase, where the droplets each have a defined droplet boundary; (D) heating the droplets sufficiently to convert the droplet boundary to a semi-solid or solid skin that encapsulates the aqueous phase; and (E) detecting PCR amplification of a nucleic acid target within the droplets.

7. The method of paragraph 6, wherein detecting PCR amplification includes optically detecting PCR amplification.

8. The method of paragraph 7, wherein optically detecting PCR amplification includes detecting a fluorescently-labeled probe.

9. The method of paragraph 6, further comprising a step of manipulating the converted droplets by one or more of transporting, sorting, focusing, diluting, concentrating, and dispensing the converted droplets.

10. The method of paragraph 9, wherein manipulating the converted droplets includes manipulating using microfluidics.

Example 5. Selected Embodiments II

This example describes selected aspects and embodiments related to assays with emulsions that include capsules, presented without limitation as a series of numbered paragraphs.

1. A method of performing an assay, comprising: (A) providing an aqueous phase including a sample and an effective concentration of one or more skin-forming proteins; (B) forming an emulsion including droplets of the aqueous phase disposed in a nonaqueous continuous phase; (C) heating the emulsion to create an interfacial skin between each droplet and the continuous phase, to transform the droplets into capsules; and (D) collecting assay data related to the sample from the capsules.

2. The method of paragraph 1, wherein the step of heating includes a step of heating the emulsion to a temperature of at least about 55° C.

3. The method of paragraph 2, wherein the step of heating includes a step of heating the emulsion to a temperature above about 90° C.

4. The method of paragraph 1, further comprising a step of amplifying a nucleic acid target in individual capsules.

5. The method of paragraph 4, further comprising a step of thermally cycling the emulsion to promote amplification of the nucleic acid target.

6. The method of paragraph 1, wherein the aqueous phase provided includes the skin-forming proteins at a concentration of at least about 0.01% by weight.

7. The method of paragraph 1, wherein the aqueous phase provided includes the skin-forming proteins at a concentration of at least about 0.03% by weight.

8. The method of paragraph 1, further comprising a step of providing an oil phase that is used as a nonaqueous continuous phase for the step of forming an emulsion, and wherein the oil phase includes a negatively-charged, fluorinated surfactant in the continuous phase.

9. The method of paragraph 1, wherein the fluorinated surfactant is present at a concentration of about 0.05% to 0.5% by weight.

10. The method of paragraph 1, wherein the capsules have a high packing density after the step of heating, and wherein the step of collecting data includes a step of collecting data from capsules traveling serially through a detection region.

11. The method of paragraph 1, wherein the step of collecting data includes a step of imaging capsules.

12. The method of paragraph 1, wherein the aqueous phase includes at least one surfactant.

13. The method of paragraph 12, wherein the surfactant is present at a concentration of about 0.01% to 5% by weight.

14. The method of paragraph 12, wherein the surfactant is present at a concentration of about 0.1% to 1% by weight.

15. The method of paragraph 12, wherein the surfactant is present at a concentration of about 0.5% by weight.

16. The method of paragraph 12, wherein the surfactant includes a block copolymer of polypropylene oxide and polyethylene oxide.

17. The method of paragraph 1, wherein the step of providing an aqueous phase includes a step of providing an aqueous phase including a surfactant and the skin-forming proteins, and wherein the surfactant is not required for creation of the interfacial skin.

18. The method of paragraph 1, wherein the aqueous phase provided includes the skin-forming proteins at a concentration of about 0.01% to 10% by weight.

19. The method of paragraph 1, wherein the aqueous phase provided includes the skin-forming proteins at a concentration of about 0.03% to 3% by weight.

20. The method of paragraph 1, wherein the aqueous phase provided includes the skin-forming proteins at a concentration of about 0.1% to 1% by weight.

21. The method of paragraph 1, wherein the skin-forming proteins are required for formation of the interfacial skin.

22. The method of paragraph 1, wherein the skin-forming proteins are selected from the group consisting of serum albumin, casein, gelatin, and globulin.

23. The method of paragraph 22, wherein the skin-forming proteins include bovine serum albumin (BSA).

24. The method of paragraph 1, wherein the step of forming an emulsion includes a step of generating droplets having an average diameter of about 1 μm to 500 μm.

25. The method of paragraph 1, wherein the step of forming an emulsion includes a step of serially generating droplets that are monodisperse.

26. The method of paragraph 1, further comprising a step of providing an oil phase including a fluorinated oil and at least one fluorinated surfactant, wherein the step of forming an emulsion includes a step of generating droplets of the aqueous phase disposed in the oil phase.

27. The method of paragraph 26, wherein the at least one fluorinated surfactant includes a fluorinated polyether.

28. The method of paragraph 26, wherein the oil phase provided includes a fluorinated surfactant at a concentration of about 0.001% to 10% by weight.

29. The method of paragraph 26, wherein the oil phase provided includes a fluorinated surfactant at a concentration of about 0.05% to 2% by weight.

30. The method of paragraph 26, wherein the oil phase provided includes a fluorinated surfactant at a concentration of about 0.05% to 0.5% by weight.

31. The method of paragraph 1, wherein the sample includes a nucleic acid target, and wherein the step of collecting assay data includes a step of collecting assay data related to amplification of the nucleic acid target in capsules of the emulsion.

32. The method of paragraph 1, wherein the step of heating the emulsion is performed with the emulsion disposed in a container that is sealed with a sealing member, further comprising a step of piercing the sealing member after the step of heating.

33. The method of paragraph 1, wherein the step of heating the emulsion is performed with the emulsion disposed in a container, further comprising a step of disposing a tip of a fluid transport device in the emulsion and a step of moving capsules from the container into the fluid transport device via the tip.

34. The method of paragraph 1, further comprising a step of driving flow of capsules through a detection region, wherein the step of collecting assay data is performed as the capsules travel through the detection region.

35. The method of paragraph 34, wherein the step of collecting assay data includes a step of collecting assay data from individual capsules traveling serially through the detection region.

36. The method of paragraph 1, wherein the step of collecting assay data includes a step of imaging capsules.

37. The method of paragraph 1, further comprising a step of driving flow of capsules in a continuous phase at a flow rate of at least about 100 µL/min.

38. The method of paragraph 1, further comprising a step of selectively removing a portion of the continuous phase after the step of forming an emulsion and before the step of heating the emulsion.

39. The method of paragraph 1, further comprising a step of placing an overlay onto the emulsion before the step of heating the emulsion.

40. The method of paragraph 39, wherein the overlay includes droplets disposed in a continuous phase.

41. The method of paragraph 40, wherein the droplets of the overlay do not interfere with the step of collecting assay data.

42. The method of paragraph 40, wherein the overlay is an aqueous phase or an oil phase that is immiscible with the continuous phase.

43. The method of paragraph 1, wherein the step of heating the emulsion is performed without an overlay on the emulsion such that the emulsion is in contact with air.

44. The method of paragraph 1, further comprising a step of adding a spacing fluid to the emulsion after the step of heating the emulsion, wherein the spacing fluid is miscible with the continuous phase.

45. The method of paragraph 44, further comprising a step of picking up capsules of the emulsion with a fluid transport device after the step of adding a spacing fluid.

46. The method of paragraph 44, wherein the spacing fluid contains no surfactant that is present at a concentration substantially above the critical micelle concentration of the surfactant.

47. The method of paragraph 44, further comprising a step of providing an oil phase that is used as a continuous phase for the step of forming an emulsion, wherein each of the oil phase and the spacing fluid has a percent by weight of surfactant, and wherein the percent by weight of surfactant in the oil phase is substantially higher than in the spacing fluid.

48. The method of paragraph 47, wherein the percent by weight of surfactant in the oil phase is at least about ten-fold higher than in the spacing fluid.

49. The method of paragraph 44, further comprising a step of providing an oil phase that is used as a continuous phase for the step of forming an emulsion, wherein the oil phase includes an ionic surfactant and the spacing fluid includes a nonionic surfactant.

50. The method of paragraph 1, further comprising (1) a step of driving flow of capsules in a carrier fluid along a flow path extending through a detection region, and (2) a step of adding a spacing fluid to the carrier fluid in the flow path to space capsules before such capsules reach the detection region.

51. The method of paragraph 50, wherein the spacing fluid contains no surfactant that is present at a concentration substantially above the critical micelle concentration of the surfactant.

52. The method of paragraph 50, further comprising a step of providing an oil phase that is used as a continuous phase for the step of forming an emulsion, wherein each of the oil phase and the spacing fluid has a percent by weight of surfactant, and wherein the percent by weight of surfactant in the oil phase is substantially higher than in the spacing fluid.

53. The method of paragraph 52, wherein the percent by weight of surfactant in the oil phase is at least about 100-fold higher than in the spacing fluid.

54. The method of paragraph 50, further comprising a step of providing an oil phase that is used as a continuous phase for the step of forming an emulsion, wherein the oil phase includes an ionic surfactant and the spacing fluid includes a nonionic surfactant.

55. A method of performing an assay, comprising: (A) providing an aqueous phase including an effective concentration of one or more skin-forming proteins; (B) providing an oil phase including a fluorinated oil and at least one fluorinated surfactant; (C) forming an emulsion including droplets of the aqueous phase disposed in the oil phase; (D) transforming the droplets into capsules by creating an interfacial skin between each droplet and the oil phase; (E) thermally cycling the capsules to amplify a nucleic acid target in individual capsules; and (F) collecting amplification data from the capsules.

56. The method of paragraph 55, wherein the aqueous phase provided includes the skin-forming proteins at a concentration of at least about 0.01% by weight.

57. The method of paragraph 55, wherein the aqueous phase provided includes the skin-forming proteins at a concentration of at least about 0.03% by weight.

58. The method of paragraph 55, wherein the oil phase provided includes a fluorinated surfactant at a concentration of about 0.05% to 0.5% by weight.

59. The method of paragraph 55, wherein the capsules have a high packing density after the step of transforming, and wherein the step of collecting amplification data includes a step of collecting amplification data from capsules traveling serially through a detection region.

60. The method of paragraph 55, wherein the step of transforming includes a step of heating the emulsion to a temperature of at least about 50° C.

61. A method of performing an assay, comprising: (A) providing an oil phase including a fluorinated oil and at least one ionic surfactant that is fluorinated and negatively-charged; (B) forming an emulsion including volumes of an aqueous phase disposed in the oil phase; (C) heating the emulsion to a temperature of at least about 50° C.; (D) amplifying a nucleic acid target in the volumes; and (E) collecting assay data related to amplification of the nucleic acid target in individual volumes.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A stabilized emulsion, comprising:
a continuous phase comprising a fluorinated oil and at least one anionic surfactant; and a plurality of capsules disposed in the continuous phase, each capsule including a proteinaceous, interfacial skin encapsulating an aqueous phase.

2. The stabilized emulsion of claim 1, wherein the anionic surfactant is a fluorinated anionic surfactant.

3. The stabilized emulsion of claim 2, wherein the fluorinated anionic surfactant is polyfluorinated or perfluorinated or both.

4. The stabilized emulsion of claim 1, wherein the anionic surfactant is a carboxylic acid-terminated perfluoropolyether, a carboxylate salt of a perfluoropolyether, or an amide or ester of a carboxylic acid-terminated perfluoropolyether.

5. The stabilized emulsion of claim 1, wherein the anionic surfactant is at a concentration of 0.02% to 10% by weight.

6. The stabilized emulsion of claim 1, wherein the continuous phase comprises a second surfactant.

7. The stabilized emulsion of claim 6, wherein the second surfactant is a fluorinated alcohol with only one or two hydroxyl groups.

8. The stabilized emulsion of claim 7, wherein the fluorinated alcohol is perfluorodecanol or perfluorooctanol.

9. The stabilized emulsion of claim 1, wherein the aqueous phase comprises a sample comprising a nucleic acid.

10. The stabilized emulsion of claim 9, wherein the aqueous phase comprises a polymerase.

11. The stabilized emulsion of claim 1, wherein the proteinaceous skin includes at least one protein selected from the group consisting of albumin, casein, gelatin, and globulin.

12. The stabilized emulsion of claim 1, wherein the plurality of capsules contain an indicator dye.

13. The stabilized emulsion of claim 1, wherein the protein is at a concentration of 0.05-2% by weight.

* * * * *